(12) United States Patent
Dessen et al.

(10) Patent No.: US 6,801,860 B1
(45) Date of Patent: Oct. 5, 2004

(54) CRYSTAL STRUCTURE OF CPLA2 AND METHODS OF IDENTIFYING AGONISTS AND ANTAGONISTS USING SAME

(75) Inventors: Andrea Dessen, Grenoble (FR); William S. Somers, Cambridge, MA (US); Mark L. Stahl, Lexington, MA (US); Jasbir S. Seehra, Lexington, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 09/250,083

(22) Filed: Feb. 15, 1999

(51) Int. Cl.$^7$ .............................. G06F 9/455; C12Q 1/44
(52) U.S. Cl. ............................... 702/27; 702/19; 435/19
(58) Field of Search ....................... 702/19, 27; 435/18, 435/19; 703/11

(56) References Cited

U.S. PATENT DOCUMENTS

| | | | |
|---|---|---|---|
| 5,221,410 A | 6/1993 | Kushner et al. | 156/600 |
| 5,322,776 A | 6/1994 | Knopf et al. | 435/69.1 |
| 5,328,842 A | 7/1994 | Chiou et al. | 435/240.2 |
| 5,354,677 A | 10/1994 | Knopf et al. | 435/198 |
| 5,466,595 A | 11/1995 | Jones et al. | 435/240.2 |
| 5,527,698 A | 6/1996 | Knopf et al. | 435/198 |
| 5,554,511 A | 9/1996 | Jones et al. | 435/69.1 |
| 5,589,170 A | 12/1996 | Jones et al. | 424/94.6 |
| 5,593,878 A | 1/1997 | Knopf et al. | 435/198 |
| 5,840,511 A | 11/1998 | Jones et al. | 435/19 |

FOREIGN PATENT DOCUMENTS

EP            0501779 A1 *   9/1992 ........... C12P/21/08

OTHER PUBLICATIONS

Protein Data Bank Acession No. 1CJY. Human Cytosolic Phospholipase A2. Deposited Apr. 20, 1999.*

Bacon, D. J., and Anderson. W. F. (1988). A fast algorithm for rendering space–filling molecule pictures. J. Mol. Graph. 6, 219–220.

Balboa, M. A. et al., (1997). Identity between the $Ca^{2+}$–independent phsopholipase $A_2$ enzymes from P388D, macrophages and chinese hamster ovary cells. J. Biol. Chem. 272, 8576–8580.

Bonventre, J. V. et al., (1997) Reduced fertility and postischaemic brain injury in mice deficient in cytosolic phospholipase $A_2$. Nature 390, 622–625.

Börsch–Haubold, A. G. et al., (1998). Identification of the phosphorylation sites of cytosolic phospholipase $A_2$ in agonist–stimulated human platelets and HeLa cells. J. Biol. Chem. 273, 4449–4458.

Bricogne, G. (1993). Direct phase determination by entropy maximization and likelihood ranking: status report and perspectives. Acta Cryst. D49, 37–60.

Brünger, A. T. et al. (1990) Slow–cooling protocols for crystallographic refinement by simulated annealing: Acta Cryst. A46, 585–593.

Brünger, A. T. (1992a). The free R value: a novel statistical quantity for assessing the accuracy of crystal structures. Nature 355, 472–474.

Clark, J. D. et al. (1991). A novel arachidonic acid–selective cytosolic $PLA_2$ contains a $CA^{2+}$–dependent translocation domain with homology to PKC and GAP. Cell 65, 1043–1051.

Clark, J. D. et al. (1995). Cytosolic phospholipase $A_2$. Lipid Mediators Cell Signalling 12, 83–117.

Cleland, W. W., and Kreevoy, M. M. (1994). Low–barrier hydrogen bonds and enzymic catalysis. Science 264, 1887–1890.

Collaborative Computing Project Number 4 (1994) "The CCP4 suite: programs for protein crystallography," Acta Crystallogr. S 760–763.

Cowtan, K. D. and Main, P. (1996). Phase combination and cross validation in iterated density modification calculations. Acta Crystallogr. D 42, 43–48.

Cygler, M. and Schrag, J. D. (1997). Structure as basis for understanding interfacial properties of lipases. Meth. Enzymol. 284, 3–27.

Dennis, E. A. (1997). The growing phospholipase $A_2$ superfamily of signal transduction enzymes. Trends Biochem. Sci. 22, 1–2.

De Carvalho, M. G. S. et al., (1996). Identification of phosphorylation sites of human 85kda cytosolic phospholipase $A_2$ expressed in insect cells and present in human monocytes. J. Biol. Chem. 271, 1–11.

Derewenda, Z. S, and Derewenda, U. (1991). Relationships among serine hydrolases: evidence for a common structural motif in triacylglyceride lipases and esterases. Biochem. Cell. Biol. 69, 842–851.

Dessen et al., "Crystal structure of human cytosolic phospholipase A2 reveals a novel topology and catalytic mechanism," Cell, 1999; 97:349–360.

Duggleby, H. J. et al. (1995). Penicillin acylase has a single–amino–acid catalytic centre. Nature 373, 264–268.

Essen, L.–O. et al. (1996). Crystal structure of a mammalian phosphoinositide–specific phospholipase C. Nature 380, 595–602.

(List continued on next page.)

Primary Examiner—Marjorie Moran
(74) Attorney, Agent, or Firm—Lahive & Cockfield, LLP; Amy E. Mandragouras, Esq.; Lisa M. DiRocco, Esq.

(57) ABSTRACT

The present invention provides for crystalline cPLA2. The crystal structure of cPLA2 has also been solved using such material. Models based upon such crystal structure are also provided. Methods of identifying inhibitors of cPLA2 activity and membrane binding using such models are also disclosed.

7 Claims, 9 Drawing Sheets

OTHER PUBLICATIONS

Glaser, K.B., "Regulation of phospholipase A2 enzyme: selective inhibitors and their pharmacological potential," *Adv. Pharm.* 1995 32:31–66.

Glover, S. et al. (1995) Translocation of the 85–kDa phospholipase $A_2$ from cytosol to the nuclear envelope in rat basophilic leukemia cells stimulated with calcium ionophore of IgE/antigen. J. Biol. Chem. 270, 15359–15367.

Grobler, J. A. et al. (1996). C2 domain conformational changes in phospholipase C. Nat. Struct. Biol. 3, 788–795.

Hanel, A. M., and Gelb, M. H. (1993). Processive interfacial catalysis by mammalian 85–kilodalton phospholipase $A_2$ enzymes on product–containing vesicles: application to the determination of substrate preference. Biochemistry 32, 5949–5958.

Hanel, A. M. et al. (1995). Multiple enzymatic activities of the human cytosolic 85–kDa phospholipase $A_2$: hydrolytic reactions and acyl transfer to glycerol. Biochemistry 34, 7807–7818.

Hattori, M. et al. (1994). The catalytic subunit of bovine brain platelet–activating factor acetylhydrolase is a novel type of serine esterase. J. Biol. Chem. 269, 23150–23155.

Hattori, M. et al. (1995). Cloning and expression of a cDNA encoding the beta–subunit (30–kDa subunit) of bovine brain platelet–activating factor acetylhydrolase. J. Biol. Chem. 270, 31345–31352.

Hendrickson, W. A. (1991). Determination of macromolecular structures from anomalous diffraction of synchrotron radiation. Science 254, 51–58.

Hendrickson, W. A. et al., (1997) "Phase determination from multiwavelength anomalous diffraction measurements," *Methods Enzymol.* 276, 494–523.

Hixon, M. S. et al. (1998). Calcium–dependent and –independent interfacial binding and catalysis of cytosolic group IV phospholipase $A_2$. Biochemistry 37, 8516–8526.

Huang, Z. et al., (1996). Functional identification of the active–site nucleophile of the human 85–kDa cytosolic phospholipase $A_2$. Biochemistry 35, 3712–3721.

Kramer, R. M. et al., (1991). The $Ca^{2+}$–sensitive cytosolic phospholipase $A_2$ is a 100–kDA protein in human monoblast U937 cells. J. Biol. Chem. 266, 5268–5272.

Kraulis, P. J. (1991). MOLSCRIPT: a program to produce both detailed and schematic plots of potein structures. J. Appl. Cryst. 24, 946–950.

Leslie, C. C. et al. (1990), Anionic phospholipids stimulate an arachidonoyl–hydrolyzing phospholipase $A_2$ from macrophages and reduce the calcium requirement for activity. Biochim. Biophys. Acta 1045, 261–270.

Leslie, C. C. (1997). Properties and regulation of cytosolic phospholipase $A_2$. J. Biol. Chem. 272, 16709–16712.

Lin. L.–L. Lin, A. Y., and DeWitt, D. L. (1992a) IL–1 induces the accumulation of cPLA2 and the release of $PGE_2$ in human fibroblasts. J. Biol. Chem. 267, 23451–23454.

Lin. L.–L., Lin, A. Y., and Knopf. J. L. (1992b) Cytosolic phospholipase $A_2$ is coupled to hormonally regulated release of arachidonic acid. Proc. Natl. Acad. Sci. USA 89, 6147–6151.

Lin. L.–L., Wartmann, M., Lin, A. Y., Knopf. J. L., Seth, A., and Davis, R. J. (1993) $cPLA_2$ is phosphorylated and activated by MAP kinase. Cell 72, 269–278.

Makino et al., "Automated flexible ligand docking method and its application for database search," *J. Comp. Chem.,* 1997; 18:1812–1825.

Matagne, A. et al. (1998). Catalytic properties of class A – lactamases: efficiency and diversity. Biochem. J. 330, 581–598.

Mosior, M. et al. (1998). Group IV cytosolic phospholipase $A_2$ binds with high affinity and specificity to phosphatidylinositol 4,5–bisphosphate resulting in dramatic increases in activity. J. Biol. Chem. 273, 2184–2191.

Nalefski, E. A. et al. (1994) Delineation of two functionally distinct domains of cytosolic phospholipase $A_2$, a regulatory $Ca^{2+}$–dependent lipid–binding domain and a $Ca^{2+}$–independent catalytic domain. J. Biol. Chem. 269, 18239–18249.

Nalefski, E. A., and Falke, J. J. (1996). The C2 domain calcium–binding motif: structural and functional diversity. Protein Sci. 12, 2375–2390.

Nalefski, E. A. et al. (1998). Independent folding and ligand specificity of the C2 caclium–dependent lipid binding domain of cytosolic phospholipase $A_2$. J. Biol. Chem. 273, 1365–1372.

Nalefski, E. A., and Falke, J. J. (1998). Location of the membrane–docking face on the $Ca^{2+}$–activated C2 domain of cytosolic phospholipase $A_2$. Biochemistry 37, 17642–17650.

O'Byrne, P. M. (1997) Leukotrienes in the pathogenesis of asthma. Chest 111, 27S–34S.

Otwinowski, Z. (1993). In Data Collection and Processing. L. Sawyer, N. Isaacs, and S. W. Bailey, eds. (Daresbury, U. K.: Science and Engineering Council), pp. 56–62.

Perisic, O. et al. (1998). Crystal structure of a calcium–phospholipid binding domain from cytosolic phospholipase $A_2$. J. Biol. Chem. 273, 1596–1604.

Pickard, R. T. et al. (1996). Identification of essential residues for the catalytic funciton of 85–dKa cytosolic phospholipase $A_2$. J. Biol. Chem. 271, 19225–19231.

Qui, Z.–H. et al. (1998). The role of calcium and phosphorylation of cytosolic phospholipase $A_2$ in regulating arachidonic acid release in macrophages. J. Biol. Chem. 273, 8203–8211.

Rao, V. D. et al. (1998). Structure of type IIbeta phosphatidylinositol phosphate kinase: a protein kinase fold flattened for interfacial phosphorylation. Cell 94, 829–839.

Reynolds, et al. (1993). Metal ion and salt effects on the phospholipase $A_2$, lysophospholipase, and transaclyase activities of human cytosolic phospholipase $A_2$. Biochim. Biophys. Acta 1167, 272–280.

Schievella, A. R. et al. (1995). Calcium–mediated translocation of cytosolic phospholipase $A_2$ to the nuclear envelope and endoplasmic reticulum. J. Biol. Chem. 270, 30749–30754.

Schrag, J. D. and Cyger, M. (1997). Lipases and hydrolase fold. Meth. Enzymol. 284, 85–107.

Scott, D. L. et al. (1990). Interfacial catalysis: the mechanism of phospholipase $A_2$. Science 250, 1541–1546.

Sharp, J. D. et al. (1991). Molecular cloning and expression of human $Ca^{2+}$–sensitive cytosolic phospholipase $A_2$. J. Biol. Chem. 266, 14850–14853.

Sharp, J. D. et al. (1994). Serine 228 is essential for catalytic activities of 85–kDa cytosolic phospholipase $A_2$. J. Biol. Chem. 269, 23250–23254.

Simon, et al. (1998) Preliminary study of the safety and efficacy of SC–58635, a novel cyclo–oxygenase 2 inhibitor: efficacy and safety in two placebo–controlled trails in osteoarthritis and rheumatoid arthritis, and studies of gastrointestinal and platelet effects. Arthritis Rheum. 41:1591–1602.

Tang, J. et al. (1997). A novel cytosolic calcium–independent phsopholipase $A_2$ contains eight ankyrin motifs. J. Biol. Chem. 272, 8567–8575.

Tjoelker, L. W. et al. (1995). Anti–inflammatory properties of a platelet–activating factor acetylhydrolase. Nature 374, 549–553.

Trimble, L. A. et al. (1993). NMR structural studies of the tight complex between a trifluoromethyl ketone inhibitor and the 85–kDa human phospholipase $A_2$. Biochemistry 32, 12560–12565.

Underwood, K. W. et al. (1998). A novel calcium–independent phospholipase $A_2$, cPLA2–, that is prenylated and contains homology to CPLA2. J. Biol. Chem. 273, 21926–21932.

Uozumi, N. et al. (1997). Role of cytosolic phospholipase $A_2$ in allergic response and parturition. Nature 390, 618–622.

Xu et al., "Solution structure and membraine interactions of the C2 domain of cytosolic phosphilipase A2," *J. Mol. Biol.*, 1998; 280:485–500.

Zhang et al., "Identification and molecular characterization of the Ca1B domain of the cytosolic phospholipase A2 (cPLA2) in human neutrophil," *Advan. Exper. Med. Biol.* 1997; 416:305–308.

* cited by examiner

FIG. 4

```
beta    480  LRELAWRLGFGPCAEECAFLSFRKQVVAALRQALQLDGDLQED---ETEVVAIMASGGG
gamma     1  MGSSEVSLIPGLQKEEKAAVERRRDHVLKALKKLMIEADEAQP-------VVCLGSGGG
alpha   139  CSCPDERFSMALCQQERTFRQQRKFEIRESMKKLLGPKNSEGLHSARDVEVVAILGSGGG
                                    α                              β4 beta    537  IRAMTSLYQLAGLRELGLLDCVMMTGASGSTNALANLYEDPEMSQKDLAGPTELLKTQ
gamma    53  LRAHIACLGVLSEMKEQGLLDAVTYAGVSGSTWAMSSLYTN----QGDMEALEAILKHR
alpha   199  FRAMIGFSLVMKALYESGLLDCATYAGLSGSTAYMSSLYSHDDFPRGPEETNEELMKN
                αB                    β5      αC               αD beta    597  VTKQKLGVLAPSQLQRYRQFLAEKARLGYPSCPNLLALINEALHDEPHHKLSDQREA
gamma   109  FTK------QEWDLAKSLQKTIQAARS-ENYSLTDFWAYMHISKQTRSLPESHLENMKKP
alpha   259  VSHNPELLEETEQKVKRYMESIWKKKSSGQPVETDLFGMLIGETPLIHNRMNFTLSSEKDK
                             αE                        αF beta    657  ISHGQNPLPLYCALNTRGQS---LKTFEDGENQEFSPYEVGLPKYGAFIPSELFGSEPPDG
gamma   162  VEEGTLPYHPLLAAIDNDLQPSWQEARAPETNFEFTPHHAGESALGAFVSITHEGSKRKKG
alpha   319  VNTAQCELDLSTCEHVAPDV---SELMFADWFSPYELGMAKYGTRMAPFLFGSKFTTG
                   β6             β7       β8    β9     β9a beta    715  QLMKRLPESRICQDLEESNLVAANLQDSLWASEP-----SQFWDEWRNQANLDKEQV
gamma   222  RLVRTHPPERDLTFLRGLNCSALGNTEVIRELIFDQLRNLLLKGLRRAMANAKSKGHLIF
alpha   376  TVVKEYEENPHRLMGVWGSAESILFIRVEGVSGSQSRGSTMEEELENFTTKHIVSNDSS
                 β9B        fa          fb             fc beta    770  P-LKTET-----PPSTAG---RIAEFFTDLAWR-----------PLAQA
gamma   282  ARINTQPSSQGEHPPEDEGGGEPEHTWLTEMENTR-----TSLEKQEQ
alpha   436  DSDDESH-------PKGTENEDAGSDQQSDNQASIHRMIMALVSDSALFNTREGRAGK
                              fd                           β9 beta    801  THN---EIRGLHFHKDYFQHE----------HFSTAKATT-----LGGEPNQLTPSEPI
gamma   328  PHEDPERKGSLSNLMDEVKKTG-----ICASKWAGTTHNFLYKHGDIRDKEMSSRKHI
alpha   489  VHN---FMLGLNLNTSYPLSPLSDFATQDSFDDDELDAAVADPDEFERIYEPLDVKSNKI
                c beta    843  CLEDVGYLINTSCLPKLQPTRENDLILSLDYNLHG-----AEQQEDLGRSCQEGGIPFD
gamma   382  HLVDAGIAINTPFLVLPPTREVHLILSFDFSAGD-----EIETIRATTDVGRRHKIPPE
alpha   546  HVADSGLTFNLPPLREQRGVDLITSFDFSARPSDSSPLEKELLAERWAKMNKPFD
             β9d               β10                      αG beta    898  PHSDSPE--EQLQPRECHTISDPIGPGA---EAVLHEPLVSDSIREKSAFGVRRTPEEI
gamma   437  QVEEAEIDLWSKIQASCLTLKGEIG------PVMIHFDLPM-----------IDACGG
alpha   606  KHDEYVPP--REGLAECYMPKPKNPDMEKDCPTTIHFVLANINTRKMKAPGVPRETEEEK
                                  β11            β12              αH beta    953  AGEVNLSSSDSP---YHYTKVTYEQPDVDKLHLTHMNVCNNQEQLIEALRQAIQRSQRIR
gamma   478  DIEANSDIYD-----FKLADTYILDVVVLAEAKKNVREKKKILREIMNVAGLYYPID
alpha   664  EIADEDIFDQPESPESTFNFQYPNQAPKREIHDMVENTLDIDVIKEMVESIEYKVQNP
                                         αI                    αJ beta   1011  PH-----------------
gamma   534  SARSCCLA-----------
alpha   724  SRCSVSLSNVEARRFFNKEFLSKPKA
```

CRYSTAL STRUCTURE OF CPLA2 AND METHODS OF IDENTIFYING AGONISTS AND ANTAGONISTS USING SAME

BACKGROUND OF THE INVENTION

Leukotrienes and prostaglandins are inflammatory mediators important in asthma, arthritis, and other inflammatory diseases. Leukotrienes cause airway obstruction in asthmatics through bronchoconstriction, increased mucus secretion, and chemoattraction of inflammatory cells (O'Byrne, 1997); prostaglandins cause pain and edema associated with arthritis. Pharmacological intervention blocking either the synthesis or action of these lipid mediators is effective in treating human disease, thus confirming their importance (Simon et al., 1998; O'Byrne, 1997).

Cytosolic phospholipase $A_2$ (cPLA$_2$) initiates the production of leukotrienes and prostaglandins by releasing arachidonic acid from cellular membranes. Arachidonic acid in turn is metabolized to prostaglandins by the cyclooxygenase pathway and to leukotrienes by the 5-lipoxygenase pathway. Concomitant with the release of arachidonic acid, lyso-platelet-activating factor (lyso-PAF) is formed, which can then be acetylated to generate PAF, a molecule also implicated in the pathophysiology of asthma and arthritis (Venable et al., 1993). Hence, the reaction catalyzed by cPLA$_2$ initiates the production of three classes of inflammatory mediators: leukotrienes, prostaglandins, and PAF.

cPLA$_2$ is a member of a diverse superfamily of phospholipase $A_2$ enzymes with the common ability to cleave the sn-2 ester of glycerophospholipids. The first members of the family to be characterized were the low molecular weight enzymes that are secreted either extracellularly or into granules (and are here collectively referred to as sPLA$_2$s; groups I, II, III, V, VII, and IX) (Dennis, 1997). The PLA$_2$ family has expanded with the cloning and characterization of calcium-dependent arachidonyl-selective cPLA$_2$ (Clark et al., 1991; Kramer et al., 1991), the calcium-independent PLA$_2$ (Tang et al., 1997; Balboa et al., 1997) and the plasma and intracellular PAF-acetylhydrolases (Hattori et al., 1994, 1995). Each of these new enzymes shares no sequence homology with the low molecular weight enzymes or with each other. In addition, unlike sPLA$_2$s, which use activated water to cleave the phospholipid, these enzymes appear to use a nucleophilic serine. In this respect, they have more in common with other lipases of the α/β hydrolase family than with the sPLA$_2$s. Two additional enzymes with 30% identity to the catalytic domain of cPLA$_2$ have recently been cloned; they have been termed cPLA$_2$β (C. Song et al., manuscript in preparation) and cPLA$_2$γ (Underwood et al., 1998).

The cloning of cPLA2 is also described in U.S. Pat. Nos. 5,322,776, 5,354,677, 5,527698 and 5,593,878. The cloning of calcium-independent cPLA2 is also described in U.S. Pat. Nos. 5,466,595, 5,554,511, 5,589,170 and 5,840,511.

Numerous pieces of evidence have supported the central role of cPLA$_2$ in lipid mediator biosynthesis. cPLA$_2$ is the only enzyme which is highly selective for phospholipids containing arachidonic acid in the sn-2 position (Clark et al., 1995; Hanel & Gelb, 1993). Activation of cPLA$_2$ or its increased expression have been linked with increased leukotriene and prostaglandin synthesis (Lin et al., 1992b). Following activation, cPLA$_2$ translocates to the nuclear membrane, where it is co-localized with the cyclooxygenase and lipoxygenase that metabolize arachidonate to prostaglandins and leukotrienes (Schievella et al., Glover et al., 1995). Although these data are compelling, the most definitive evidence for the central role of cPLA$_2$ in eicosanoid and PAF production came from mice made deficient in cPLA$_2$ through homologous recombination (Uozumi et al., 1997; Bonventre et al., 1997). Peritoneal macrophages derived from these animals failed to make leukotrienes, prostaglandins, or PAF. The cPLA$_2$ deficient mice have also been informative of the role of cPLA$_2$ in disease, since these mice are resistant to bronchial hyperreactivity in an anaphylaxis model used to mimic asthma (Uozumi et al., 1997).

cPLA$_2$ consists of at least two functionally distinct domains: a N-terminal $Ca^{2+}$-dependent lipid-binding (CaLB) domain and a $Ca^{2+}$-independent catalytic domain (Nalefski et al., 1994). The N-terminal CaLB domain is a member of the C2 family and its structure has been solved (Perisic et al., 1998; Xu et al., 1998); it mediates calcium regulation by co-localizing the catalytic domain with its membrane substrate (Nalefski et al., 1994). cPLA$_2$ activity, in addition, is also regulated by phosphorylation of the catalytic domain (Lin et al., 1991; Leslie, 1997). Ser505 (of SEQ ID NO:2) and Ser727 (of SEQ ID NO:2) are conserved across all species and are phosphorylated in multiple cell types (de Carvalho et al., 1998). Phosphorylation of Ser505 (of SEQ ID NO:2) by members of the MAP-kinase family is a common response to extracellular stimuli that release arachidonic acid. Mutation of Ser505 (of SEQ ID NO:2) to Ala decreases activation (Lin et al., 1993) whereas the analogous mutation on Ser727 (of SEQ ID NO:2) has no effect (Leslie, 1998).

Several lines of evidence suggest that the catalytic mechanism of cPLA$_2$ proceeds through a serine-acyl intermediate (Trimble et al., 1993; Hanel & Gelb, 1995). Mutation of Ser228 (of SEQ ID NO:2) abolishes cPLA$_2$ activity against all substrates including phospholipids, lysophospholipids, and fatty acylated coumarin (Pickard et al., 1996; Huang et al., 1996). Ser228 (of SEQ ID NO:2) is present in a pentapeptide sequence, G-L-S-G-S (SEQ ID NO:3), which is similar to the classic "lipase motif" G-X-S-X-G (Schrag & Cygler, 1997) found in most lipases within the broader family of enzymes called the α/β hydrolases. These enzymes possess a common core which consists of a well-conserved mixed β sheet whose strands are interspersed by α helices. In all α/β hydrolases, the catalytic serine is present in a tight turn between a β-strand and an α-helix, termed the "nucleophilic elbow" (see review by Schrag & Cygler, 1997). This turn directs the short serine side chain away from the protein backbone, reducing the steric hindrance about the residue and requiring that the +2 and −2 sidechains be small to avoid steric clash; thus the prevalence of the G-X-S-X-G motif (Derewenda & Derewenda, 1991).

In addition to serine, α/β hydrolases use a histidine and an acid (aspartate/glutamate) as the other members of a catalytic triad simliar to that present in serine proteases (Schrag & Cygler, 1997). However, although in cPLA$_2$ Asp549 (of SEQ ID NO:2) was shown to be essential for activity, none of the 19 histidine residues were (Pickard et al., 1996). A different residue, Arg200 (of SEQ ID NO:2), was implicated as playing a role in the enzymatic process, although the mechanism for its involvement remained unknown. These observations suggested that cPLA$_2$ acts through a novel catalytic mechanism for acyl hydrolases.

Like both the sPLA$_2$s and the lipases of the α/β hydrolase family, cPLA$_2$ preferentially cleaves substrates presented in an interface (Nalefski et al., 1994). This phenomenon, known as interfacial activation, has been attributed to either conformational changes in the enzyme or more favorable presentation of the substrate (Scott et al., 1990). The origin of the 1500-fold difference in cPLA$_2$ activity toward monomeric and micellar substrate remains unknown.

Despite the key role of cPLA$_2$ in inflammatory disease, its three-dimensional structure remained unsolved, leaving numerous questions unanswered. Here we report the x-ray crystal structure of human cPLA$_2$ at 2.5 Å resolution. The structure provides insight into the origin of arachidonate selectivity and interfacial activation, clarifies the roles of Ser228, Asp549, and Arg200 (of SEQ ID NO:2), and reveals the interplay between CaLB and the catalytic domains. Importantly, the structure is of a unique topology, distinct from that of the α/β hydrolase family.

SUMMARY OF THE INVENTION

All references to amino acids in cPLA2 herein are made using residue numbers which refer to the cPLA2 sequence found in SEQ ID NO:2 and in Table I of U.S. Pat. No. 5,527,698, with the first methionine being designated residue 1 (Met1). SEQ ID NO:2 is encoded by the nucleotide sequence set forth in SEQ ID NO:1.

The present invention provides for crystalline cPLA2. Preferably, the cPLA2 is either human cPLA2 or cPLA2 from a non-mammalian species. In certain embodiments, the cPLA2 is recombinant cPLA2 and/or comprises the mature sequence of naturally-occurring cPLA2.

Other embodiments provide for a crystalline composition comprising cPLA2 in association with a second chemical species. Preferably, the second chemical species is selected from the group consisting of a potential inhibitor of cPLA2 activity and a potential inhibitor of cPLA2 membrane binding.

Yet other embodiments provide for a model of the structure of cPLA2 comprising a data set embodying the structure of cPLA2. Preferably, such data set was determined by crystallographic analysis of cPLA2, including possibly by NMR analysis. In certain embodiments, the data set embodies a portion of the structure of cPLA2, including without limitation the active site of cPLA2 or the CaLB domain of cPLA2.

Any available method may be used to construct such model from the crystallographic and/or NMR data disclosed herein or obtained from independent analysis of crystalline cPLA2. Such a model can be constructed from available analytical data points using known software packages such as HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, RASMOL, and CHAIN. The model constructed from these data can then be visualized using available systems, including, for example, Silicon Graphics, Evans and Sutherland, SUN, Hewlett Packard, Apple Macintosh, DEC, IBM, and Compaq. The present invention also provides for a computer system which comprises the model of the invention and hardware used for construction, processing and/or visualization of the model of the invention.

Further embodiments provide a computer system comprising computer hardware and the model of the present invention.

Methods are also provided for identifying a species which is an agonist or antagonist of cPLA2 activity or binding comprising: (a) providing the model of the present invention, (b) studying the interaction of candidate species with such model, and (c) selecting a species which is predicted to act as said agonist or antagonist. Species identified in accordance with such methods are also provided.

Other embodiments provide: (1) a process of identifying a substance that inhibits cPLA2 activity or binding comprising determining the interaction between a candidate substance and a model of the structure of cPLA2, or (2) a process of identifying a substance that mimics cPLA2 activity or binding comprising determining the interaction between a candidate substance and a model of the structure of cPLA2. Substances identified in accordance with such processes are also provided.

The study of the interaction of the candidate species with the model can be performed using available software platforms, including QUANTA, RASMOL, O, CHAIN, FRODO, INSIGHT, DOCK, MCSS/HOOK, CHARMM, LEAPFROG, CAVEAT(UC Berkley), CAVEAT(MSI), MODELLER, CATALYST, and ISIS.

Other embodiments provide a method of identifying inhibitors of cPLA2 activity by rational drug design comprising: (a) designing a potential inhibitor that will form non-covalent bonds with one or more amino acids in the cPLA2 active site based upon the crystal structure co-ordinates of cPLA2; (b) synthesizing the inhibitor; and (c) determining whether the potential inhibitor inhibits the activity of cPLA2. Preferably, the crystal structure co-ordinates of cPLA2 used in such methods are obtained from a cPLA2 crystal of space group $P2_12_12$ with a=153.59 angstroms, b=95.49 angstroms, and c=139.13 angstroms. In other preferred embodiments, the inhibitor is designed to interact with one or more atoms of said one or more amino acids in the cPLA2 active site is selected from the group consisting of:

CB and Oγ atoms of Ser228 of SEQ ID NO:2;

Oδ1 and O δ2 atoms of Asp549 and Asp575 of SEQ ID NO:2;

CB, CG, CD, NE, CZ, NH1 and NH2 atoms of Arg200, Arg413 and Arg579 of SEQ ID NO:2;

Backbone carbonyl oxygen of Trp393 of SEQ ID NO:2;

Nδ2 and Oδ1 atoms of Asn555 of SEQ ID NO:2;

Atoms CD1, CE1, CG, CZ, CE2, and CD2 of Phe397, Phe681, Phe683 and Phe199 of SEQ ID NO:2;

CG, CD1, NE1, CE2, CZ2, CH2, CZ3, CE3 and CD2 of Trp232 and Trp393 of SEQ ID NO:2;

CB and Oγ atoms of Ser577 of SEQ ID NO:2;

Atom s CB and Sγ of Cys331 of SEQ ID NO:2;

Atoms OE1 and OE2 of Glu589 of SEQ ID NO:2;

Atoms CB, CG, CD, CE and NZ of Lys588 of SEQ ID NO:2;

Oγ1 atom of Thr680 of SEQ ID NO:2;

OE1 and OE2 atoms of Glu418 and Glu422 of SEQ ID NO:2;

Atoms CB, CG, SD and CE of Met417 of SEQ ID NO:2;

Atoms CB, CG, CD1 and CD2 of Leu400 and Leu421 of SEQ ID NO:2;

Atoms CB, CG1, CG2, or CD1 of Ile424 of SEQ ID NO:2;

Backbone NH and carbonyl oxygen atoms of Ala578 of SEQ ID NO:2; and

Atoms CB, CG, ND1, CE1, NE2, and CD2 of His639 of SEQ ID NO:2.

Agonists and antagonists identified by such methods are also provided.

Methods are also provided for identifying inhibitors of cPLA2 membrane binding by rational drug design comprising: (a) designing a potential inhibitor that will form non-covalent bonds with one or more amino acids in the cPLA2 electrostatic patch region based upon the crystal structure co-ordinates of cPLA2; (b) synthesizing the inhibitor; and (c) determining whether the potential inhibitor inhibits the membrane binding of cPLA2. Preferably, the crystal structure co-ordinates of cPLA2 used in such methods are obtained from a cPLA2 crystal of space group $P2_12_12$ with a=153.59 angstroms, b=95.49 angstroms, and c=139.13 angstroms. In other preferred embodiments, the inhibitor is designed to interact with one or more amino acids selected from the group consisting of Arg467, is Arg485, Lys488, Lys544 and Lys543 (all of SEQ ID NO:2). Agonists and antagonists identified by such methods are also provided.

BRIEF DESCRIPTION OF THE DRAWINGS

The patent contains at least one drawing executed in color. Copies of this patent with color drawings will be provided by the Office upon request and payment of the necessary fee.

(B) GRASP surface diagram of $cPLA_2$. Residues which presented $N^{15}/NH$ shifts upon interaction with dodecylphosphocholine micelles in NMR experiments by Xu et al. (1998) are colored purple. The $cPLA_2$ active cleft is highlighted in red. Lid residues have been removed for clarity.

(C) Surface potential representation of $cPLA_2$, with basic residues in blue shades and acidic residues in red. The lid residues have been removed for clarity. A highly basic patch is clearly visible on the membrane-binding region of the molecule. Figure prepared with GRASP (Nicholls, 1992). All views are in the same orientation.

Figure 3A:
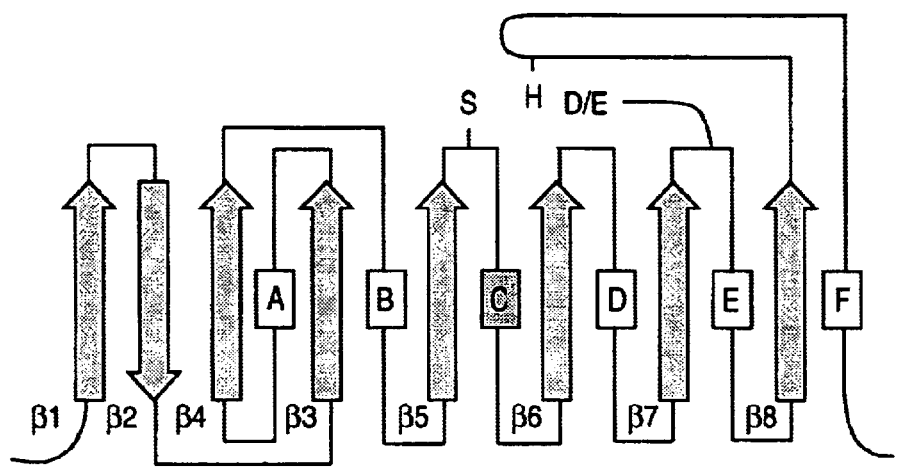

FIG. 3(A) Richardson representation of the canonical α/β hydrolase fold. β strands are represented as arrows, while at helices are rectangles. Secondary structural element numbering is according to the review by Schrag & Cygler (1997). Helix C, which immediately follows the "nucleophilic elbow", is colored pink.

(B) Richardson diagram of the $cPLA_2$ fold. The numbering scheme was devised so that the helix immediately following Ser288 of SEQ ID NO:2 is Helix C, as in the canonical α/β hydrolase fold. The central core is colored yellow for a more facile comparison with the canonical α/β hydrolase fold in (A). Elements composing the "cap" are colored purple; loop regions in red are highly mobile and do not present traceable electron density.

FIG. 4. Primary structure alignment of $cPLA_2$ α, β, and γ. Identical residues are boxed, while the secondary structural elements observed in the x-ray crystal structure of cPLA2 α are indicated below the sequences. Secondary structural elements outside of the cap region are shown in yellow, while those in the cap region are shown in purple. Black lines represent areas of turns or loops. Residues not identified with black lines or secondary structural elements do not display traceable electron density.

Figure 5A:
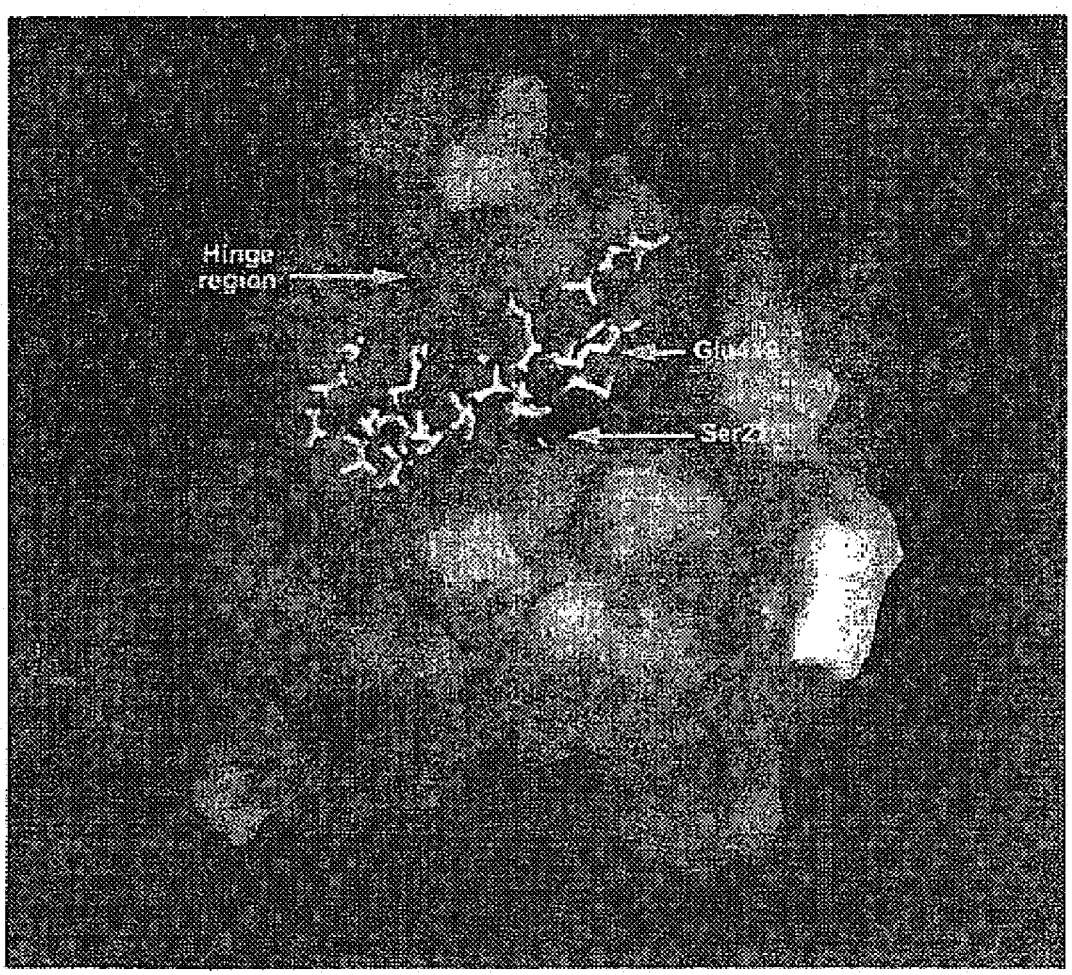

FIG. 5(A). Surface diagram showing the catalytic domain of $cPLA_2$ covered by the lid residues. Ser228 of SEQ ID NO:2 is shown at the bottom of the funnel. The continuation of the sequence which is not visible in experimental maps is represented by red dots and is proposed to be involved in the formation of a lid hinge. Residues for which only the backbone atoms are visible in electron density maps are represented as alanines. Exposed surfaces of all hydrophobic residues have been colored blue, and that of Arg200 of SEQ ID NO:2 has been colored red. The figure was prepared with GRASP (Nicholls, 1992).

(B) Close-up of the active site of $cPLA_2$ in a 7 Å radius around Ser228 of SEQ ID NO:2. The two residues involved directly in catalysis are colored green. Arg200 of SEQ ID NO:2 and the loop harboring Gly residues 197 and 198 of SEQ ID NO:2 are shown in yellow. A single water molecule visible in the experimental maps hydrogen bonds with Asp549 of SEQ ID NO:2 and carbonyl atoms from Trp393 of SEQ ID NO:2 and Thr330 of SEQ ID NO:2. Figure generated with Molscript and RASTER3D.

Figure 6:
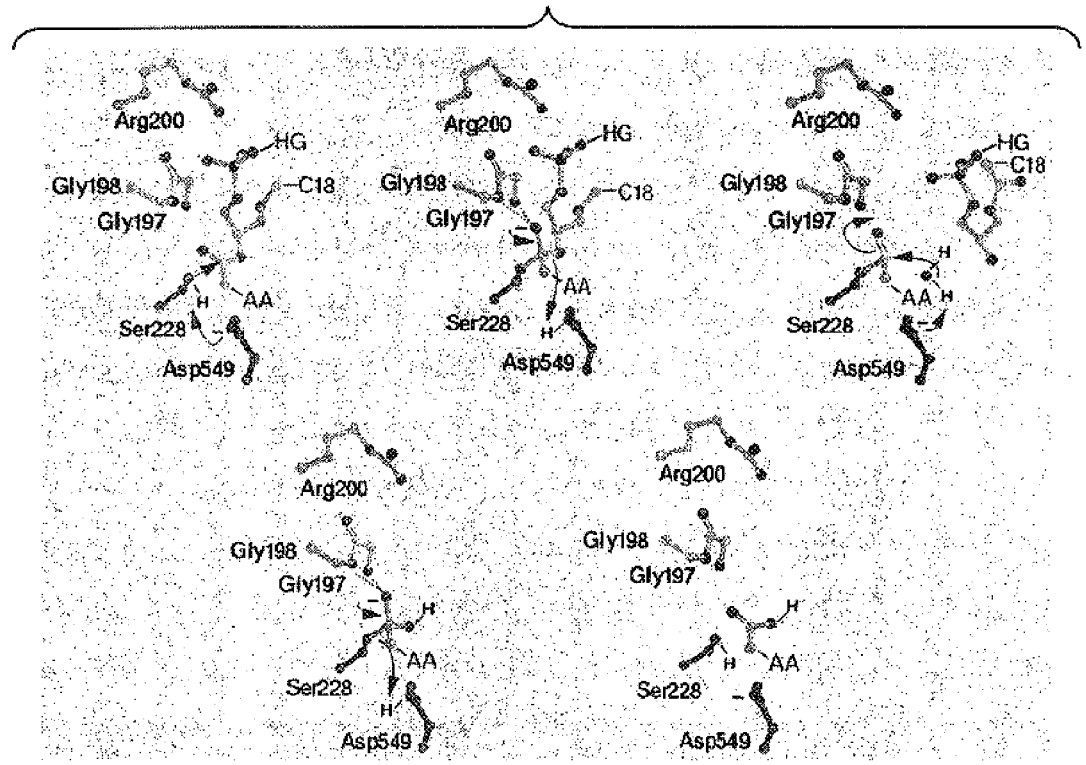

FIG. 6. Catalytic mechanism proposed for $cPLA_2$, involving the attack of Ser228 of SEQ ID NO:2 on the sn-2 position of the glycerophospholipidic substrate. AA: arachidonic acid; HG: head group; C18: octadecyl group. Gly 197 of SEQ ID NO:2 and 198 of SEQ ID NO:2 are suggested as being part of the oxyanion hole, while Arg200 of SEQ ID NO:2 stabilizes the phosphate moiety of the head group.

DETAILED DESCRIPTION OF THE INVENTION AND PREFERRED EMBODIMENTS

The structure of $cPLA_2$ was solved by employing one heavy atom scatterer per 749 residues (corresponding to SEQ ID NO:2)

Full length human $cPLA_2$ was expressed in CHO cells and purified by modification of the methodology described in Clark et al., 1990 (Stahl et al., manuscript in preparation). Crystals were obtained at 18° C. using PEG 1000 as a precipitant and employing standard vapor diffusion techniques. Single crystals grew within a few days to dimensions of up to 0.6 mm×0.5 mm×0.1 mm but were highly susceptible to x-ray damage. Rounds of crystal soaking into cryoprotectant solutions with increasing amounts of PEG 400 and DMSO, followed by flash cooling and exposure to synchrotron radiation, were critical in obtaining diffraction to a minimum Bragg spacing of 2.5 Å. Crystals are of space group $P2_12_12$ (a=153.59 Å, b=95.49 Å, c=139.13 Å), with two monomers (1498 residues) and 60% solvent per asymmetric unit.

Attempts to prepare heavy atom soaked crystals of $cPLA_2$ revealed that only gadolinium or terbium could provide isomorphous derivatives. Either lanthanide, however, replaced a single $Ca^{2+}$ atom in CaLB, thus providing a single heavy atom scatterer per 749 amino acid residues. In-house phasing information from these crystals was not of high enough quality to produce an initial electron density map. This observation, added to the fact that binding of most heavy atoms generated non-isomorphism between native and soaked crystals, led to an effort to solve the structure of $cPLA_2$ by multiwavelength anomalous dipersion (MAD) phasing (Hendrickson, 1991).

Figure 1:
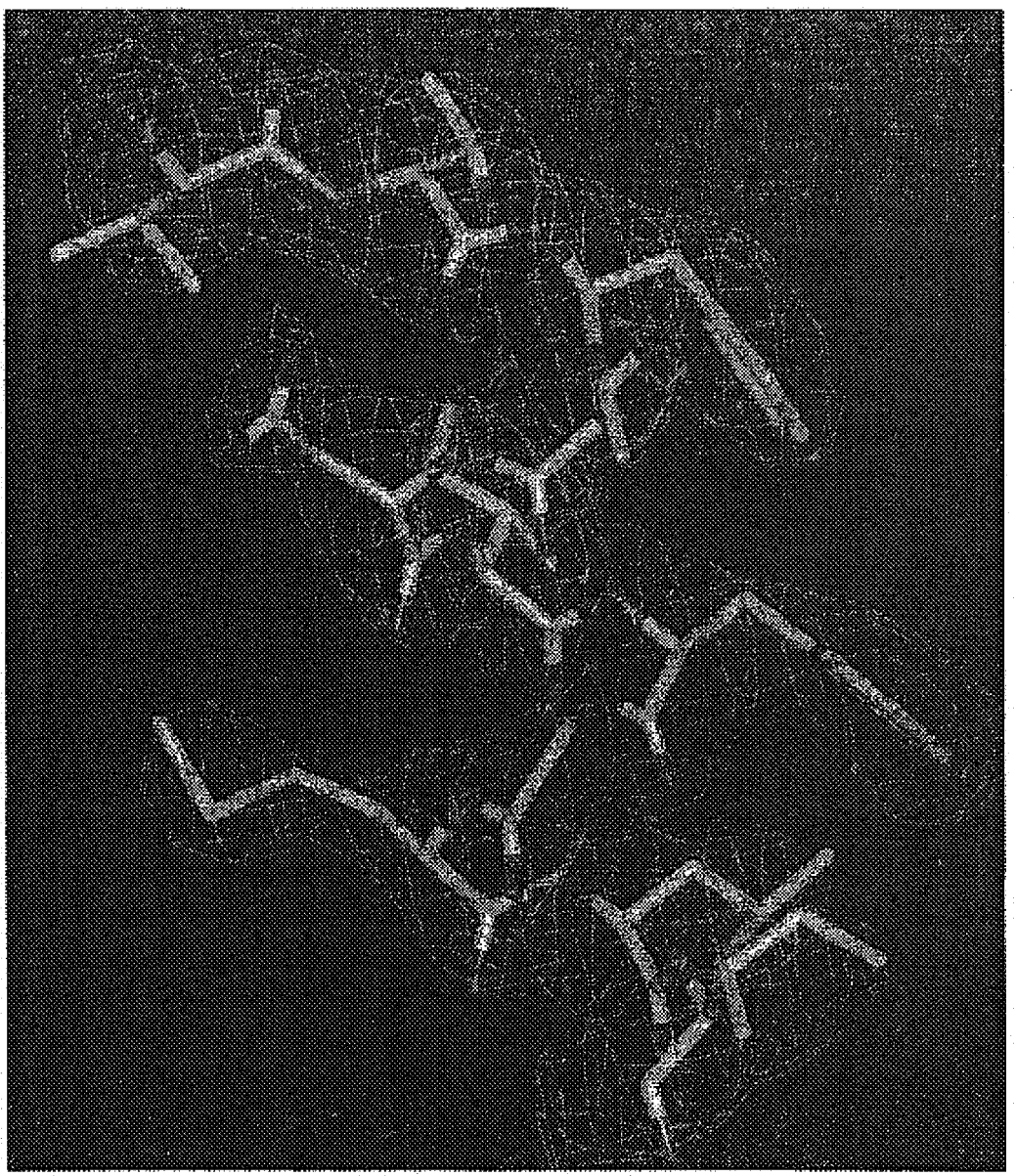
FIG. 1. Experimental map generated with MAD phases obtained from scattering of a single Tb atom per 749 residues of cPLA2 (SEQ ID NO:2). Solvent flattening (60% solvent content) and 2-fold non-crystallographic symmetry averaging in DM were employed for map generation.

Terbium-soaked $cPLA_2$ crystals were prepared, cryotreated (see Methods), and cooled in a 100° K nitrogen stream. Data at three different wavelengths around the Tb $L_{III}$ edge (see Table I) were collected from a single crystal which, due to radiation sensitivity, was translated along its rotation axis between data collections. Experimental phases to 3.2 Å were calculated with SHARP (de La Fortelle & Bricogne, 1997); subsequently, several cycles of solvent flattening and two-fold averaging in DM (Cowtan et al., 1996) allowed us to extend phases to 2.5 Å. This procedure generated a high quality electron density map (FIG. 1) in which both domains of each $cPLA_2$ monomer could be clearly identified. Initially, CaLB (Perisic et al., 1998; 1RLW) was rotated into density and a polyalanine trace was built for the visible regions of the catalytic domain using the program QUANTA (Molecular Simulations Inc.) generating a model with approximately 550 residues for each monomer. Phase restrained refinement of this initial structure with a final phase combination step (REFMAC; Murshudov et al., 1997) followed by manual model building (QUANTA) generated a model which was subsequently refined in XPLOR (Brünger et al., 1992b). The present model contains 1285 residues (between both monomers) and 40 water molecules (Table I).

Molecular Structure

Figure 2A:
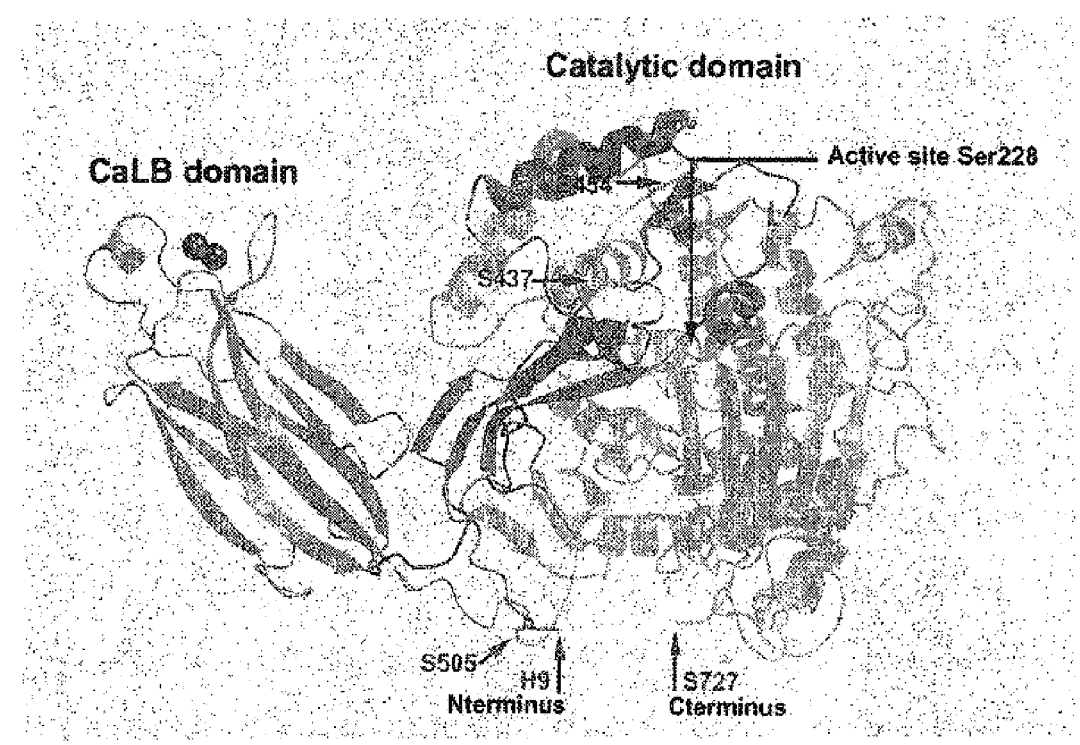
FIG. 2(A). Ribbon diagram of the $cPLA_2$ monomer. The CaLB domain is shown in green, with the two $Ca^{2+}$ atoms depicted in red. The "cap" structure of $cPLA_2$ is colored purple. Mobile loops with poor electron density are shown as dots. The flexible linker between CaLB and the catalytic domain is colored red. The positions of the 4 serine residues which are phosphorylated in $cPLA_2$ are also shown. Figure prepared with Molscript (Kraulis, 1991) and RASTER3D (Bacon & Anderson, 1988).
Figure 2B:
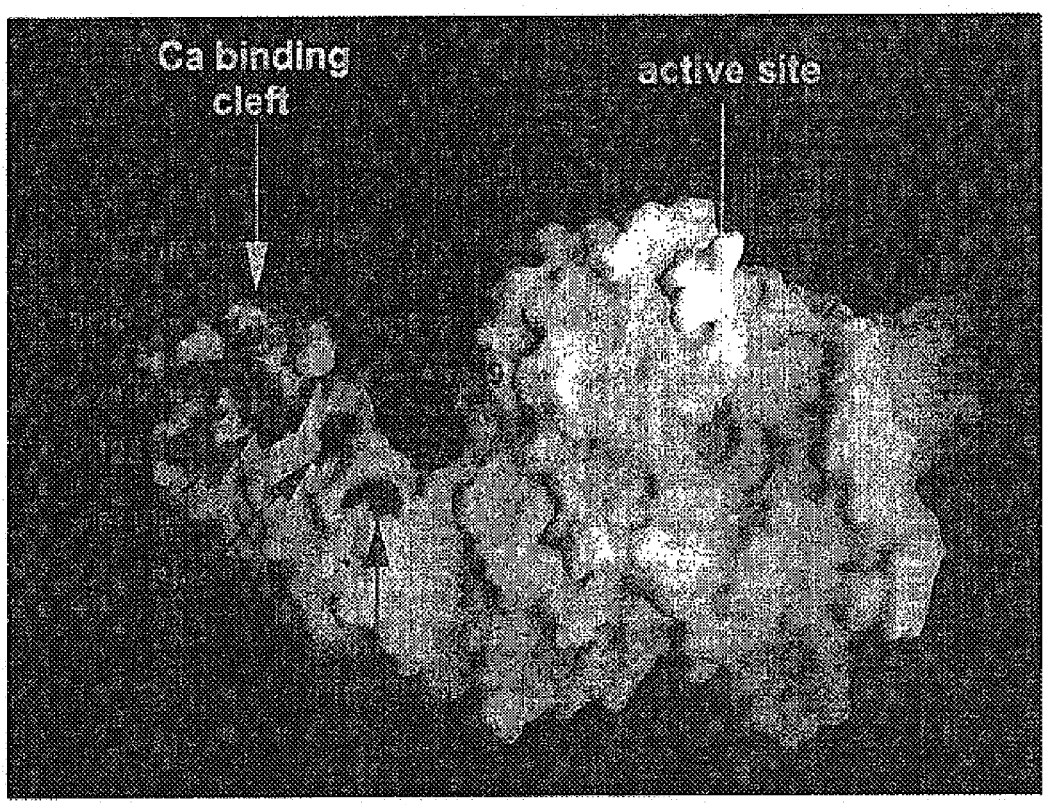

The cPLA$_2$ monomer is a two domain ellipsoidal structure with dimensions of ~100 Å×55 Å×45 Å (FIG. 2a). The N-terminal CaLB domain (residues 16–138 of SEQ ID NO:2) is a distinctly folded β sandwich, connected by residues 139–143 of SEQ ID NO:2 to the catalytic domain, with which it forms very few protein-protein contacts. The central core of the catalytic domain is composed of a 10-strand central β sheet with interspersed helices which is distinct from the canonical α/β hydrolase fold. The cPLA$_2$ monomers present in the asymmetric unit are not perfectly superimposable due to flexibility of the interdomain loop. Indeed, when the CaLB domains are superimposed, there is a 4–5° difference between the two catalytic domains. The loop which interconnects the domains has a distinct conformation in each monomer and its residues display high temperature factors.

cPLA$_2$ is a cytosolic protein which translocates to the membrane when free levels of Ca$^{2+}$ are raised to submicromolar levels (Clark et al., 1990, 1991). The domain arrangement of cPLA$_2$ suggests how the active site is oriented with respect to the cellular membrane. FIG. 2b is a surface diagram which highlights results of HSQC studies performed on CaLB by Xu and co-workers (1998). Residues which displayed N$^{15}$/NH shifts upon incubation with dodecylphosphocholine micelles in these experiments are highlighted in purple. It is clear that the highlighted residues appear on the same face of the molecule as the active site. Consequently, if CaLB employs these residues to associate with a phospholipid membrane, the catalytic domain is roughly positioned to bind a phospholipid substrate in the active site. The flexibility of the linker between the two domains as well as the lack of major protein-protein interactions between them suggests that a small rotation between domains can be accomplished for optimal interactions with the membrane.

Figure 2C:
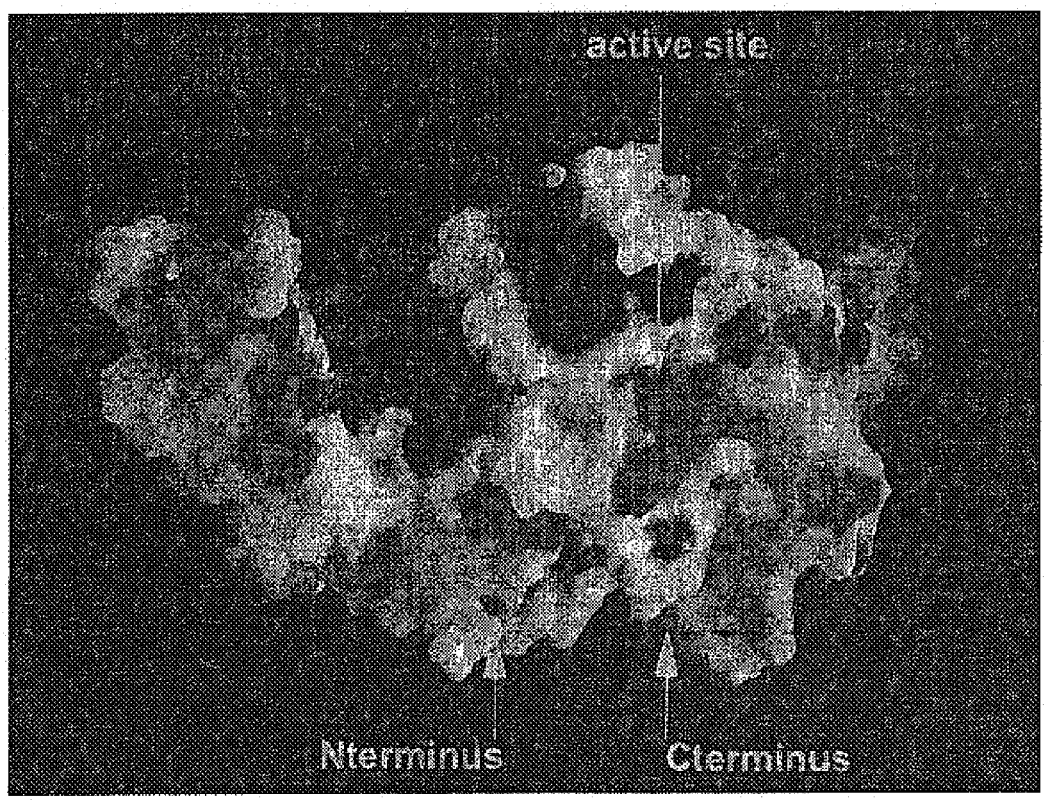

As shown in the surface potential diagram in FIG. 2c, there exists a highly basic region which extends from the active site through a strip of positively charged residues on the β3 strand of CaLB. This basic characteristic would be expected of a region in the protein making multiple electrostatic contacts with the negatively-charged phospholipid head groups of the membrane layer (see below). Residues 434 to 456 of SEQ ID NO:2, however, are disordered, making it impossible to accurately define the true size of the basic patch. Nevertheless, it is noteworthy that similar basic patches were seen in PI4 kinase and in different species of sPLA$_2$s (Rao et al., 1998). It is tempting to suspect that the high affinity binding of cPLA$_2$ to membranes made of phosphatidyl methanol liposomes (Hixon & Gelb, 1998) is mediated through this patch and the nearby basic stretch of β strand 3 in the CaLB domain.

The N-terminal CaLB Domain

The structure of the CaLB domain in full-length cPLA$_2$ is very similar to those solved by NMR and x-ray crystallography (Xu et al., 1998; Perisic et al., 1998), with minor differences. Briefly, it consists of eight antiparallel β strands interconnected by six loops, folding into a β-sandwich which fits the "type II" topology for C2 domains (Nalefski et al., 1994b). Two Ca$^{2+}$ atoms are bound at one end of CaLB through a constellation of Asp and Asn side chains, as well as backbone carbonyl atoms, on three distinct loops (calcium-binding loops; CBLs); the same atomic arrangement has been observed in the CALB domain solved by Perisic and co-workers (1998). The Ca$^{2+}$ atoms are approximately 4 Å apart. The environment of the Ca$^{2+}$ atoms in full-length cPLA$_2$, however, does not display any of the water molecules present in the CaLB structure solved by these authors; instead, coordinated to calcium site 1 (defined in Perisic et al., 1998) is a molecule of MES (2-[N-morpholino] ethanesulfonic acid) from the buffer employed in crystallization and cryoprotection. In both cPLA$_2$ monomers, the distance between Ca$^{2+}$ 1 and the closest MES sulfonate oxygen atom is approximately 2.2 Å. In addition, the morpholino group is also in contact with the side chains of His 62 of SEQ ID NO:2 and Tyr96 of SEQ ID NO:2, thus forming a small hydrophobic niche. Although a crystallization artifact, the coordination of Ca$^{2+}$ 1 of cPLA$_2$ to the sulfate of MES could be emulating the binding mode of the phosphate group of a phospholipid molecule, thus suggesting that, in cPLA$_2$, Ca$^{2+}$ acts as a bridge between the protein and the phosphorylated membrane rather than solely as an allosteric activator.

The Novel Topology of the cPLA$_2$ Fold Distinguishes it from α/β Hydrolases

Figure 3B:
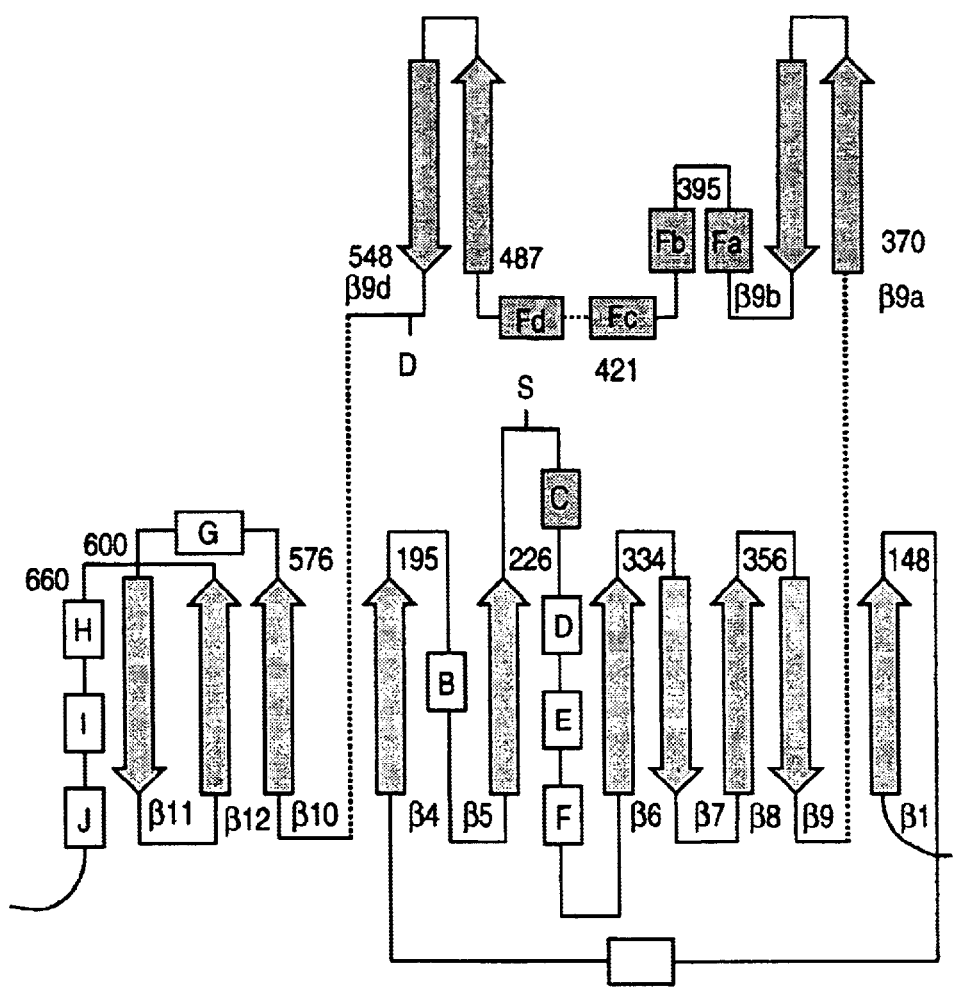

The catalytic domain of cPLA$_2$ is composed of 14 β strands and 13 α helices; its central core consists of a 10-stranded central mixed β sheet surrounded by 9 α helices with strands β5 through β11 forming the most obvious portion of the sheet (refer to the Richardson diagram in FIG. 3b). The β sheet has a superhelical twist. For simplicity, the secondary elements of cPLA$_2$ have been identified based on the α/β hydrolase fold nomenclature presented by Schrag & Cylger (1997), in which the catalytic serine is always preceded by β5 and followed by Helix C.

The first β strand in the cPLA$_2$ core is β1, which follows the flexible connection after CaLB. A long loop containing one long helix makes the connection to β4, in the central part of the fold. This β1/α-helix construction is analogous to the one observed in Humicola lanuginosa lipase, where the helical region is also not considered part of the fold but connects its β10 to the first β strand in the core (entry 1TIB in the PDB). The following parallel β strand, β5, precedes the catalytic serine (228 of SEQ ID NO:2). The topologies of β5, Helix C (colored pink in FIGS. 3a and 3b), and of the loop which connects them are similar in α/β hydrolases. This interconnecting loop is termed the "nucleophilic elbow. Three more α-helices, interwoven by loops, provide the connection between this region and the further 4 β strands of this part of the fold. Of the four β strands that follow (β6–β9), β6 is the longest, making few hydrogen bonds with β7. Strands β7 to β1, therefore, although not contiguous in sequence, can be considered a small β sheet within a larger structure.

After β9 there is a major divergence from formation of the central α/β core. The cPLA$_2$ sequence at this point forms the region shown in purple in FIGS. 2a and 3b. This 180-residue patch forms a catalytic domain "cap". Asp549 of SEQ ID NO:2, the catalytic partner of Ser228 of SEQ ID NO:2, lies in the region between the end of the cap and β10, which is part of the central core. Following the cap structure, the last three β strands are positioned as to complete the central β sheet and are interspersed by helices G to J.

The α/β hydrolase fold is common to many esterases and other hydrolytic enzymes (Schrag & Cygler, 1997). Its Richardson diagram (FIG. 3a) consists of a central β sheet whose order of β strands follows the sequence linearly (with the exception of β3, which is often placed between β4 and β5). At first glance, the topology of cPLA$_2$ appears to be a circular permutation of the α/β hydrolase fold. However, a careful comparison of FIGS. 3a & 3b clearly reveals that only the region encompassing the nucleophilic elbow is in fact directly comparable (β5 to Helix C; residues 222–238 of SEQ ID NO:2). Major distinctions include the antiparallel nature of strands β6 to β9, the multiplicity of helices between β5 and β6, and the absence of intervening helices between strands of the latter part of the cpla2 α/β core.

Although the cap structure in cPLA$_2$ (residues 370–548 of SEQ ID NO:2) is part of the catalytic domain, it is not included in the α/β core. Sequence comparisons of the catalytic domains of human cPLA$_2$s α, β, and γ (FIG. 4) show that homology is concentrated within the α/β core (yellow elements) and β strands 9a and 9d. Thus, the central part of the cap is distinct among cPLA$_2$ isoforms. A comparison between the ribbon diagram of cPLA$_2$ in FIG. 2a, in which the cap region is displayed in purple, and the surface potential diagram in FIG. 2c, reveals that the highly basic region hypothesized above as making electrostatic contacts with membrane phospholipids is in fact formed in large part by cap residues.

The cap region of cPLA$_2$ also contains two of the three most mobile regions of the entire structure, residues 433–456 of SEQ ID NO:2 and 500–536 of SEQ ID NO:2 (the third region is the C-terminus, residues 728–749 of SEQ ID NO:2). These amino acid stretches do not have traceable electron density and are not included in the model (dotted lines in FIG. 2a). Interestingly, it is these highly flexible regions of the cap which harbor three of the four serine residues that become phosphorylated upon agonist stimulation (437, 454, 505 of SEQ ID NO:2). The role of Ser437 of SEQ ID NO:2 and Ser454 of SEQ ID NO:2 is unclear, since they are not conserved among different species. In contrast, Ser505 of SEQ ID NO:2 is conserved in cPLA$_2$ from evolutionarily distinct species (chicken, human, zebrafish, murine, rat), and its phosphorylation by MAP kinase is required for maximal activation of cPLA2 in insect cells (Lin, et al., 1993; Qiu et al., 1998). Ser505 of SEQ ID NO:2, which in our crystals is likely to be heterogeneously phosphorylated and is located in a highly flexible, solvent exposed loop, makes no contacts either with the body of the protein or other neighboring cPLA$_2$ monomers in the lattice. Ser505 of SEQ ID NO:2 is distal to both the active site and the membrane-binding region (see FIG. 2a); nevertheless, its proximity to the hinge between CaLB and the catalytic domain is noteworthy (see discussion). The fourth site of cPLA2 phosphorylation, Ser727 of SEQ ID NO:2, is at the C-terminus of the structure. Although this site is conserved among species, its functional relevance is not yet known.

The Active Site Funnel is Partially Covered by a Solvent-accessible Lid

The most remarkable feature of the cPLA$_2$ structure is the active site funnel, which penetrates one third of the way into the catalytic domain to reveal Ser228 of SEQ ID NO:2 and Asp549 of SEQ ID NO:2 placed at the bottom of a deep, narrow cleft. Although wide at the top, the funnel narrows down to an approximate diameter of 7 Å at the mouth of the active site cleft visible in FIG. 5a. The funnel is lined with hydrophobic residues (blue in FIG. 5a) and forms a cradle into which fatty acyl moieties of membrane phospholipid substrates may bind.

The cPLA$_2$ active site is partially covered by a "lid" composed of residues 413–457 of SEQ ID NO:2. The lid folds into a loop region, followed by a small helical stretch and a short turn (see FIG. 5a). Residues 408–412 of SEQ ID NO:2, which lead into the lid region, display very large temperature factors, and residues 434–456 of SEQ ID NO:2 do not possess traceable electron density. These observations suggest that these regions are highly mobile and could be envisioned as a "lid hinge". The visible region of the lid has an amphipathic character; its solvent exposed face is formed primarily by polar residues (T416, E418, E419, E420, N423 of SEQ ID NO:2), while the inner side is lined with hydrophobic amino acids (M417, L421, I424 of SEQ ID NO:2). It is conceivable that the "double-sided" character of the lid comes into play upon membrane phospholipid binding, since one face has the capability of forming hydrogen-bonding contacts while the other is more apt for hydrophobic interactions, either with the substrate or the membrane.

Attempts to model a diacylphospholipid molecule in the active cleft of cPLA$_2$ with the lid in place demonstrated that the acyl ester bond cannot be positioned in the vicinity of the active site serine without the generation of clashes with surrounding residues. Consequently, it is conceivable that the generation of appropriate space for substrate binding requires lid movement, a proposal in agreement with the observation that cPLA$_2$ displays greater activity in the presence of micellular rather than monomeric substrates (Cygler & Schrag, 1997), a phenomenon known as interfacial activation.

Most lipases display interfacial activation as a result of a conformational rearrangement of a lid that covers the active site in the "closed" form of the enzyme. The lid moves away upon binding of micelles, thereby generating the "open" form, in which catalytic residues are exposed to the substrate. X-ray crystallography has yielded multiple examples of this activation mechanism through the determination of structures of lipases both in "closed" and "open" forms, the latter for the most part crystallized in the presence of inhibitors (Cygler & Schrag et al., 1997). It is probable that the interfacial activation mechanism of cPLA$_2$ is comparable to that of other lid-containing lipases, in that lid movement is a key step in increasing the accessible surface area of the active site funnel as well as providing unhindered access to the catalytic residues.

The cPLA$_2$ Active Site Contains a Catalytic Dyad

Acyl hydrolysis by α/β hydrolases is performed by a (Ser-Asp/Glu-His) catalytic triad reminiscent of the one present in serine proteases. The substrate's acyl ester bond is attacked by the nucleophilic serine, generating a covalently bound acyl-enzyme intermediate that is subsequently released following a step that involves the attack of a water molecule. Although all lipid-metabolizing enzymes with the α/β hydrolase fold proceed via the use of a catalytic triad, the identification of all members of such a triad in cPLA$_2$ proved to be a challenging task. Site-directed mutagenesis by Sharp and co-workers (1994) confirmed the role of Ser228 of SEQ ID NO:2 and Asp549 of SEQ ID NO:2 in catalysis; the failure of any of the 19 histidine residues to affect activity, however, pointed to a novel catalytic mechanism (Pickard et al., 1996). These observations led many to propose that cPLA$_2$ contains a novel catalytic center which does not require the participation of histidine, while the relevance of Arg200 of SEQ ID NO:2 for activity remained unknown (Leslie, 1997; Pickard et al., 1996).

Figure 5B:
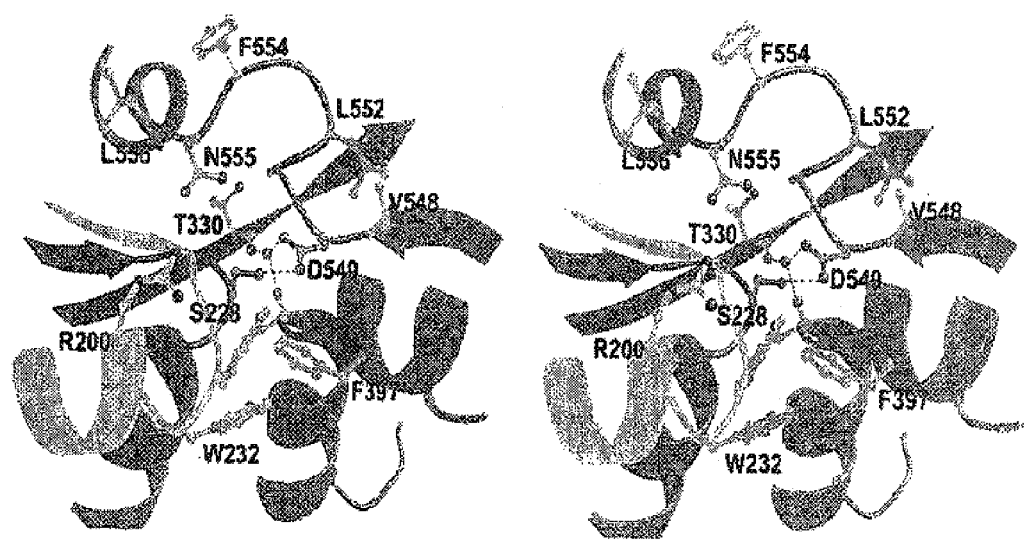

The x-ray crystal structure of cPLA$_2$ clearly reveals an active site in which Ser228 of SEQ ID NO:2 sits at the bottom of a funnel-shaped cavity; the O□2 of Asp549 of SEQ ID NO:2 lies at a distance of 2.9 Å from its O□ atom (FIG. 5b). It is clear, however, that the active site of cPLA$_2$ lacks a histidine residue. In addition, there are no other residues in a 6 Å range that could fulfill the function of active site base. All polar contributions in a range of 3.5 Å away from either residue are made by backbone groups or by a lone water molecule positioned 3.2 Å away from the O□1 atom of Asp549 of SEQ ID NO:2. Although Asn555 of SEQ ID NO:2 lines the active site funnel, its N□2 atom is approximately 6 Å away from either residue and would not be the ideal candidate to fulfill this function.

In acyl hydrolases, upon attack on the sn-2 position of a glycerophospholipidic substrate, the transition state requires stabilization by an "oxyanion hole", or a set of hydrogen bond donors (usually amide atoms) and/or basic residues with the function of stabilizing the developing negative charge of the transition state. In several lipases, at least one of the residues which contribute to the oxyanion hole is part of a moving loop, and the proper conformation is only attained when the lipase is in "open" form; this rearrangement, however, is not an absolute requirement. In cPLA$_2$, Gly197 and 198 of SEQ ID NO:2 are part of a glycine-rich flexible loop between β4 and Helix B; this positioning allows the amide backbones of Gly197 of SEQ ID NO:2 and Gly198 of SEQ ID NO:2 to be good candidates for members of a pre-formed oxyanion hole (see FIG. 5b). In addition, the backbone amide group of Gly229 of SEQ ID NO:2, which is at the apex of the turn between β5 and Helix C, also points in the direction of the Gly197 of SEQ ID NO:2 loop and therefore may also be part of the hole. Consequently, this region, much like the oxyanion hole in chymotrypsin, appears to be well-designed to stabilize the tetrahedral intermediate generated by the nucleophilic attack of the ester.

A multiplicity of roles has been suggested for Arg200 of SEQ ID NO:2. It has been implicated in providing assistance to CaLB in binding the enzyme to the lipid interface; interacting with the phospholipid membrane; participating as a catalytic residue; stabilizing an acyl-enzyme intermediate: or associating with the phosphoryl group of the substrate phospholipid (Pickard et al., 19%). The positioning of Arg200 of SEQ ID NO:2 imbedded within the funnel (its surface area is colored red in FIG. 5a) precludes it from providing any lipid binding assistance to CaLB. In addition, its side chain is approximately 9 Å away from the active site serine, which prevents it from playing a role in catalysis. Arg200 of SEQ ID NO:2, however, makes several key contacts with residues around the active site funnel. The side chain makes a salt bridge with Thr680 of SEQ ID NO:2 and contacts backbone atoms of Phe678 of SEQ ID NO:2, both of which lie in the loop between helices H and I. The location of Arg200 of SEQ ID NO:2 on the oxyanion hole loop suggests that the lack of these two hydrogen bonds in the Arg200 Lys mutant reported by Pickard & co-workers (1996) could be responsible for subtle alterations on the conformation of the oxyanion hole loop with dramatic consequences on activity.

Catalysis by cPLA$_2$ Proceeds Via a Mechanism Distinct from that of Other Acyl Hydrolases The absence of a histidine residue or any other potential base in the active site of cPLA$_2$ suggests that the enzyme promotes acyl hydrolysis via a novel catalytic mechanism. In serine proteases and other hydrolases, a histidine residue accepts a proton from the hydroxyl group of the reactive serine, thus facilitating formation of the covalent tetrahedral intermediate. In a second step, the acyl-enzyme intermediate is hydrolyzed by a water molecule to release the product, restoring the ser-hydroxyl to the enzyme. Class A TEM-1 β lactamase, whose catalytic pathway also involves the acylation of an active site serine followed by the hydrolysis of the ester bond, transfers a proton from the active site Ser70 of SEQ ID NO:2 to the carboxylate group of Glu166 of SEQ ID NO:2, either directly (Gibson et al., 1990) or via a water molecule (Lamotte-Brasseur et al., 1991). More recent studies (Damblon et al., 1996) have suggested that the long distance between the carboxylate oxygens of Glu166 of SEQ ID NO:2 and Ser70 of SEQ ID NO:2 precludes direct proton transfer, but propose the participation of a bridging water molecule for proton relay. In the catalytic mechanism of penicillin acylase (Duggleby et al., 1995), which contains a single residue catalytic center composed of the N-terminal serine, a bridging water mediates the basic character of the α-amino group of Ser1 of SEQ ID NO:2. As a consequence, the Oγ atom of Ser1 of SEQ ID NO:2 has its nucleophilicity sufficiently enhanced by the amino-terminal group, and formation of the acyl-enzyme intermediate ensues.

In cPLA$_2$, the only residue capable of playing the role of general base is Asp549 of SEQ ID NO:2 since there are no other side chains in a radius of 3.5 Å of the Oγ atom of Ser228 of SEQ ID NO:2. FIG. 6 displays a proposed model for the catalytic mechanism of cPLA$_2$. Once the enzyme is bound to the membrane, a single phospholipid molecule binds at the active site. The phosphate moiety of the head group (HG in FIG. 6) is stabilized by the Arg200 of SEQ ID NO:2 side chain. An oxyanion hole formed by the backbone amide groups of Gly197 of SEQ ID NO:2 and Gly198 of SEQ ID NO:2 is also shown polarizing the sn-2 ester and stabilizing the tetrahedral intermediate formed in panel B. Following formation of the enzyme-substrate complex, Asp549 of SEQ ID NO:2 acts as the catalytic base and abstracts a proton from the hydroxyl group of the reactive Ser228 of SEQ ID NO:2, which attacks the sn-2 ester and forms the acyl enzyme via the stabilized tetrahedral intermediate. The acyl enzyme is subsequently hydrolyzed by a water molecule (panel C) to yield free lyso-phospholipid and, after collapse of the double bond of the arachidonyl intermediate, free arachidonic acid (AA in FIG. 6; panels D and E). cPLA$_2$ may then dissociate from the membrane interface or bind another phsopholipid substrate and repeat the cycle. Thus, cPLA$_2$ is a third distinct example of an acylase which uses a nucleophilic serine without a complete catalytic triad.

Discussion

Despite the large asymmetric unit (1498 amino acids) and the fragility of cPLA$_2$ crystals, MAD phasing was successful in producing a high quality electron density map from data obtained from a single crystal. Central to this success were the large Bijvoet and dispersive differences typical of the L$_{III}$ edge of a lanthanide atom, coupled to the high flux and wavelength stability of the Advanced Light Source (Berkeley, Calif.). With the advent of third generation synchrotrons, MAD should be routinely employed for the solution of large macromolecular structures.

cPLA$_2$ is essential for the biosynthesis of lipid mediators of inflammation, as demonstrated by the use of cPLA$_2$ deficient mice (Bonventre et al.,1997; Uozumi et al., 1997). Since leukotrienes, prostaglandins and PAF play significant roles in the pathophysiology of diseases of major public impact, it is imperative to understand how their biosynthesis is regulated. The structure of cPLA$_2$ provides new insights into the origin of arachidonyl selectivity and the regulation by phosphorylation. In addition, it identifies both a new fold and mechanism for lipases. The structure of cPLA$_2$ is only the second one in which a C2 domain is seen in the context of the entire protein. Significant differences are seen between PLCδ1 and cPLA$_2$.

The cPLA$_2$ fold clearly shows that the enzyme consists of two distinct, independently folded domains. This result was not unexpected based on earlier work in which the CaLB and catalytic domains were fully functional when expressed independently. However, what was surprising was the sparsity of contacts and potential flexibility between the domains. Although C2 domains are commonly observed in signaling molecules, to date only the crystal structure of PLCδ1 has reported a C2 domain present in the context of the catalytic domain (Essen et al., 1996). In this case, extensive hydrophobic contacts exist between almost the entire surface of one face of the C2 domain and the catalytic domain. In contrast, the interactions between the catalytic and CaLB domains of cPLA$_2$ are sufficiently limited that the conformations of the polypeptide linking the two in the different monomers of the asymmetric unit are distinct. This observation is of mechanistic importance in that the optimal orientation of the CaLB and catalytic domains is not fixed, but instead may be regulated in some fashion. It is interesting to note that although the region of the protein including Ser-505 of SEQ ID NO:2, which is essential for optimal activity in cells, is disordered, this important MAP-kinase site located near the hinge region.

The detailed comparison of the structure of cPLA$_2$ and the classic α/β hydrolase fold clearly argues that cPLA$_2$ contains a novel topology. However, as noted earlier, the β hairpin containing the active site serine is structurally analogous to "nucleophilic elbow" of the α/β hydrolase fold. A Blast search of the cPLA$_2$ catalytic domain shows an extended region of homology among PLBs and cPLA$_2$ at, and y which includes residues ~190–232 of SEQ ID NO:2. This homology is of functional significance in that it contains Arg 200 of SEQ ID NO:2, the backbone regions comprising the oxyanion hole as well as the novel GXSXS lipase motif in which the second serine replaces the classic glycine. The "concentration" of homology in the short region is also explained by the genomic structure, where these residues are encoded by a single exon (which corresponds to residues 186–238 of SEQ ID NO:2).

Instead of containing a catalytic triad of Ser, His, Asp/Glu as seen for the α/β hydrolases, cPLA$_2$ cleaves the sn-2 ester using a dyad composed of Ser-228 of SEQ ID NO:2 and Asp-549 of SEQ ID NO:2. The carboxylate of Asp-549 of SEQ ID NO:2 is the only residue in sufficiently close proximity to activate the serine for nucleophilic attack. A similar catalytic dyad has been proposed for the amide hydrolysis reaction catalyzed by the Class A β-lactamases (Matagne et al., 1998). In this case, however, the glutamate side chain activates the serine residue via an intervening water molecule. Although it is difficult to assess the comparable efficiency of a dyad vs. a triad, it is noteworthy that it is the activation energy required to reach the transition state which is important in catalysis. Therefore, the stabilization due to an effective oxyanion hole can offset a less nucleophilic serine. In this crystal structure, the backbone amide group of glycines 197 of SEQ ID NO:2 and 198 of SEQ ID NO:2, positioned a mere two residues from the critical Arg-200 of SEQ ID NO:2, are appropriately positioned to act as the oxyanion hole. The backbone NH of Gly-229 of SEQ ID NO:2 could possibly also aid in stabilizing the oxyanion developing in the transition state and present in the tetrahedral intermediates. The effectiveness of the oxyanion hole is consistent with NMR studies where arachidonyltrifluoromethyl ketone appeared to bind to the enzyme as the ionized hemiketal.

The catalytic serine of cPLA$_2$ is present in a deep funnel near the center of the catalytic domain. Attempts to model the phospholipid into the active site demonstrated that the current conformation of the active site funnel was not large enough. Therefore, we propose that the somewhat mobile lid, whose C-terminus is linked to a completely disordered stretch of 23 amino acids, may move upon membrane binding, thus providing a larger accessible volume near the top of the funnel to accommodate the substrate. The crystal structures of pancreatic lipase/colipase both in the presence and absence of substrate/detergent micelles provide precedent for this model (van Tilbeurgh et al., 1993). In this case, a dramatic conformational change occurs in the presence of micelles or inhibitors entailing a lid movement of as much as 29 Å to expose the active cleft and a hydrophobic patch. Such large structural modifications have been noted for other hydrolase proteins. This conformational change upon membrane surface binding has been used to explain the process of interfacial activation, in which the catalytic activity of a lipase is orders of magnitude greater toward a substrate presented in a micelle rather than as a monomer.

In the case of cPLA$_2$, its lysophospholipase has been used compare its activity toward the same substrate presented either as a monomer or as part of a micelle. Such measurements have revealed that cPLA$_2$ activity increases ~1500-fold as the concentration of 1-palmitoyl-2-lysophosphatidylcholine increases by only 10-fold; thus, cPLA$_2$ is much more active toward substrates presented as a surface. Our structure suggests that a conformational change, dictated by movement of the flexible lid, occurs upon membrane binding; this observation is consistent with the previously observed interfacial activation.

In addition to the movement of lids covering the active sites, several structures have shown that the oxyanion hole that stabilizes the transition state is only fully formed in the presence of bound substrate or inhibitor (Cygler & Schrag, 1997). Cutinase is an exception to this general rule in that the oxyanion hole is fully formed in the native structure. Importantly, cutinase does not show interfacial activation (Martinez et al., 1992).

The selectivity of cPLA$_2$ for arachidonyl-containing phospholipids is a distinguishing feature. The low molecular weight sPLA$_2$s do not distinguish among different fatty acids, whereas cPLA$_2$ shows high selectivity for arachidonyl and other fatty acids with cis-double bonds at the 5 and 8 positions in numerous assay formats (Clark et al., 1995; Gelb aasn-1 and sn-2, Gelb hydrazin). Prior to the determination of the structure, the origin of cPLA$_2$ selectivity was unknown. It was conceivable that the catalytic machinery was located near the surface of the enzyme where it could act on the sn-2 ester without extracting the lipid from the bilayer. This would be analogous to the flattened kinase domain of PI4 kinase where the enzyme is thought to work on the lipid headgroup without extracting the phospholipid itself (Rao et al., 1998). In the case of cPLA$_2$ we would anticipate the selectivity to be due to greater exposure of the sn-2 ester due to looser packing of the polyunsaturated fatty acid. However, as we see in the structure, the phospholipid must bind ~8–10 Å into the deep active site. Thus the selectivity must be due to interactions between the arachidonyl moiety and enzyme. It will be informative to mutate the residues which are distinct between □ and □ cPLA$_2$s, namely in the active site and the completely non-conserved lid region, to determine differences in selectivity.

Preferred Methods of Administration and Dosing of Substances Identified in Accordance with the Invention As used herein, "phospholipase enzyme activity" means positive activity in an assay for metabolism of phospholipids (preferably one of the assays described in Example 2 below or described in any of the references incorporated herein). A compound has "phospholipase enzyme inhibiting activity" when it inhibits the activity of a phospholipase (preferably cPLA$_2$) in any available assay (preferably an assay described below in Example 2) for enzyme activity. In preferred embodiments, a compound has (1) an IC$_{50}$ value of less than about 25 µM in the LysoPC assay; (2) an IC$_{50}$ value of less than 50 µM in the vesicle assay; and/or (3) an IC$_{50}$ value of less than about 1 µM in the PMN assay.

Compounds of the present invention and ursolic acid are useful for inhibiting phospholipase enzyme (preferably cPLA$_2$) activity and, therefore, are useful in "treating" (i.e., treating, preventing or ameliorating) inflammatory or inflammation-related conditions (e.g., rheumatoid arthritis, psoriasis, asthma, inflammatory bowel disease, and other diseases mediated by prostaglandins, leukotrienes or PAF) and other conditions, such as osteoporosis, colitis, myelogenous leukemia, diabetes, wasting and atherosclerosis.

The present invention encompasses both pharmaceutical compositions and therapeutic methods of treatment or use which employ compounds of the present invention.

Compounds of the present invention may be used in a pharmaceutical composition when combined with a pharmaceutically acceptable carrier. Such a composition may also contain (in addition to a compound or compounds of the present invention and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, IL-1, IL-2, IL-3, IL4, IL-5, IL-6, IL-7, IL8, IL-9, IL-10, IL-11, IL12, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with compounds of the present invention, or to minimize side effects caused by the compound of the present invention. Conversely, compounds of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of a compound of the present invention is administered to a mammal having a condition to be treated. Compounds of the present invention may be administered in accordance with the method of the invention either alone or in combination with other therapies such as treatments employing other anti-inflammatory agents, cytokines, lymphokines or other hematopoietic factors. When co-administered with one or more other anti-inflammatory agents, cytokines, lymphokines or other hematopoietic factors, compounds of the present invention may be administered either simultaneously with the other anti-inflammatory agent(s), cytokine(s), lymphokine(s), other hematopoietic factor(s), thrombolytic or anti-thrombotic factors, or sequentially. If administered sequentially, the attending physician will decide on the appropriate sequence of administering compounds of the present invention in combination with other anti-inflammatory agent(s), cytokine(s), lymphokine(s), other hematopoietic factor(s), thrombolytic or anti-thrombotic factors.

Administration of compounds of the present invention used in the pharmaceutical composition or to practice the method of the present invention can be carried out in a variety of conventional ways, such as oral ingestion, inhalation, or cutaneous, subcutaneous, or intravenous injection.

When a therapeutically effective amount of compounds of the present invention is administered orally, compounds of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% compound of the present invention, and preferably from about 25 to 90% compound of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of compound of the present invention, and preferably from about 1 to 50% compound of the present invention.

When a therapeutically effective amount of compounds of the present invention is administered by intravenous, cutaneous or subcutaneous injection, compounds of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to compounds of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of compound(s) of the present invention in the pharmaceutical composition of the present invention will depend upon the nature and severity of the condition being treated, and on the nature of prior treatments which the patient has undergone. Ultimately, the attending physician will decide the amount of compound of the present invention with which to treat each individual patient. Initially, the attending physician will administer low doses of compound of the present invention and observe the patient's response. Larger doses of compounds of the present invention may be administered until the optimal therapeutic effect is obtained for the patient, and at that point the dosage is not increased further. It is contemplated that the various pharmaceutical compositions used to practice the method of the present invention should contain about 0.1 $\mu$g to about 100 mg (preferably about 100 :g to about 50 mg, more preferably about 100 :g to about 5 mg) of compound of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the compounds of the present invention will be in the range of 12 to 24 hours of continuous intravenous administration. Ultimately the attending physician will decide on the appropriate duration of intravenous therapy using the pharmaceutical composition of the present invention.

EXAMPLE 1

Protein Production, Crystallization and Data Collection

Full-length human cPLA$_2$ (residues 1–749 of SEQ ID NO:2) was cloned into vector pMT2-EMC-cPLA2 and transfected into CHO cells. The resulting cell line, E5-CHO, was grown in α medium (Gibco) containing 10% (v/v) dialyzed fetal calf serum and 10 μM methotrexate as described in Lin et al. (1992). The cell pellet was typically lysed in pH 9.0 buffer and cPLA$_2$ in the supernatant was subsequently precipitated with (NH4)$_2$SO$_4$. Multiple steps including affinity and size exclusion chromatography yielded protein samples which were suitable for crystallization experiments. A typical yield from a 100 g pellet would be 15–25 mg of pure cPLA$_2$.

Crystals of cPLA$_2$ were obtained by vapor diffusion at 18° C. using PEG 1000 as a precipitant using 12 mg/ml protein. Typically, plate-like crystals appeared overnight and continued to grow to a maximum size of 0.6 mm×0.5 mm×0.1 mm within one week. Native and heavy atom-soaked crystals were cryoprotected by transferring into increasing amounts of PEG 400 and DMSO. Heavy atom-modified crystals were prepared by soaking native crystals overnight in cryosolution with CaCl$_2$ replaced by 250 μM GdCl$_2$ or TbCl$_2$. Cryoprotected crystals were flash cooled in a liquid nitrogen stream at 100 K prior to data collection.

Diffraction data of the native, Gd- and Tb-soaked cPLA$_2$ crystals were collected at beamline 5.0.2 at Advanced Light Source using a Quantum 4 CCD detector (Area Detector Systems). Due to crystal sensitivity, the first image of each data set was analyzed with STRATEGY (R. Ravelli) in an effort to calculate the minimum amount of data collection required for a complete data set. After the determination of the optimal starting point, data was collected through a 90° sweep, after which the crystals were rotated to a position 180° from the starting point and a second 90° sweep was collected with a view towards maximizing Bijvoet pair accumulation. Crystals started displaying radiation sensitivity after approximately 100° of data collection, making it necessary to translate them along the rotation axis between wavelength changes. This methodology proved to be successful in that data sets collected from three different wavelengths displayed similar statistics. All data were collected at 100K and processed with DENZO/SCALEPACK (Otwinowski, 1993). Heavy atom sites—Both Tb sites were identified by visual inspection of anomalous Patterson maps using diffraction data collected at the peak wavelength of the Tb L$_{III}$ edge (see Table I), confirming results from previous lower resolution Tb and Gd data sets collected on an in-house Raxis IV detector (Molecular Structure Corp.). Heavy atom parameter refinement and phasing were accomplished with SHARP (de la Fortelle & Bricogne, 1997). Density modification was performed in SOLOMON (CCP4) as implemented in SHARP. The high quality experimental 3.2 Å electron density map allowed for the positioning of the entire CaLB domain as well as the initial tracing and sequence assignment of the catalytic domain (QUANTA); this procedure facilitated the calculation of a mask encompassing the protein region, which was included in further calculations. These included histogram matching (Zhang and Main, 1990), two-fold non-crystallographic symmetry averaging, and phase extension from 3.2 to 2.5 Å using the native diffraction data in DM (Cowtan et al., 1996). Cycles of phase combination and refinement were performed with REFMAC (Murshudov et al., 1997), generating a map in which most of the model could be identified, including central residues of the flexible lid.

Refinement—Cycles of rebuilding as well as positional and thermal parameter refinement in XPLOR (Brünger, 1992b) were used to improve the model, which was submitted to simulated annealing refinement (12–2.5 Å) after the Rfree had dropped below 32% (Brünger et al., 1992a). Subsequent model-building stages were performed with the aid of omit maps generated through maximum-likelihood refinement as implemented in BUSTER (Bricogne, 1993). Refinement also included a uniform bulk solvent correction (Bsol=23.8 Å$^2$; ksol=0.305 e$^-$/Å$^3$) and the application of non-crystallographic symmetric restraints. All diffraction data with F>2.0 were used throughout the refinement except for a 10% randomly selected test set which was used for calculation of Rfree. Fo-Fc maps were used to locate water molecules, which were placed at sites which displayed densities>3.0☐ and exhibited reasonable protein-solvent hydrogen-bonding distances without steric conflict. The final model contains 1285 residues (molecule A: 9–433, 456–500, and 537–727 of SEQ ID NO:2) and 40 water molecules, and exhibits good stereochemistry, with an average bond length and bond-angle deviation from ideal geometry of 0.010 Å and 1.38°, respectively. The overall free R-value is 29.7% and the R value is 24.3% using diffraction data between 12 and 2.5 Å (Table I).

TABLE I

Statistics for data collection, phase determination and refinement

| Data collection | Native | Peak | Inflection | Descending edge |
|---|---|---|---|---|
| Wavelength (Å) | λ = 1.20 | λ$_1$ = 1.64902 | λ$_2$ = 1.64963 | λ$_3$ = 1.64834 |
| Max. resolution (Å) | 2.5 | 3.4 | 3.3 | 3.2 |
| Rsym (%) | 6.4 | 11.2 | 10.3 | 9.0 |
|  | (30.0) | (41.5) | (37.1) | (38.6) |
| % completeness | 93.3 | 99.6 | 99.7 | 99.6 |
|  | (87.9) | (99.4) | (99.5) | (99.5) |
| Total reflections | 271686 | 195666 | 213851 | 233142 |
| Unique reflections | 66223 | 54331$^e$ | 59265$^e$ | 64885$^e$ |
| <I/σ(I)> | 18.2 | 9.9 | 12.3 | 13.3 |
|  | (3.3) | (2.6) | (3.3) | (2.8) |
| f' (e-) |  | −9.89 | −17.50 | −1.86 |
| f" (e-) |  | 31.90 | 18.63 | 19.24 |

| MAD phasing | | | | | | | | | |
|---|---|---|---|---|---|---|---|---|---|
| Resolution limits (Å) | 9.67 | 6.70 | 5.44 | 4.69 | 4.18 | 3.81 | 3.53 | 3.37 | overall |
| Phasing power | | | | | | | | | |
| λ$_2$ | 3.26 | 4.08 | 3.65 | 2.84 | 2.07 | 1.48 | 1.11 | 0.93 | 2.24 |
| λ$_1$ isomorphous | 1.20 | 1.15 | 1.05 | 0.83 | 0.75 | 0.68 | 0.63 | 0.53 | 0.83 |

TABLE I-continued

Statistics for data collection,
phase determination and refinement

| | | | | | | | | | |
|---|---|---|---|---|---|---|---|---|---|
| $\lambda_1$ anomalous | 3.25 | 4.26 | 3.89 | 3.18 | 2.37 | 1.70 | 1.30 | 1.21 | 2.59 |
| $\lambda_3$ isomorphous | 0.98 | 1.20 | 1.24 | 1.32 | 1.39 | 1.39 | 1.35 | 1.28 | 1.30 |
| $\lambda_3$ anomalous | 3.18 | 4.01 | 3.58 | 2.99 | 2.30 | 1.66 | 1.26 | 1.07 | 2.34 |
| mean FOM | 0.77 | 0.75 | 0.70 | 0.63 | 0.55 | 0.44 | 0.35 | 0.29 | 0.51 |

Model refinement

| | |
|---|---|
| Resolution (Å) | 12.0–2.5 |
| Rfactor (%) | 24.3 |
| Rfree (%) | 29.7 |
| <B-value> (Å$^2$) | 40.7 |

R.m.s deviations from ideal geometry

| | | | | | |
|---|---|---|---|---|---|
| Bonds (Å) | 0.007 | Angles (°) | 1.38 | B-values (Å$^2$) | 8.6 |

Rsym=$\Sigma|I_h-<I_h>|/\Sigma I_h$ where $<I_h>$ is the average intensity over symmetry equivalents.

£Friedel pairs separate.

Phasing power=$\Sigma|FH|/\Sigma||F_{PHobs}|-|F_{PHcalc}||$.

R=$\Sigma||F_o|-|F_c|/\Sigma|F_o|$, where Rfree is calculated for a randomly chosen 10% of reflections and Rfactor is calculated for the remaining 90% of reflections (F>2.0) used for structure refinement.

Coorardinates will be deposited at the Brookhaven Protein Databank.

EXAMPLE 2

Activity Assays (a) Vesicle Assay 1-palmitoyl-2-[$^{14}$C] arachidonyl phosphotidylcholine (58 mCi/mmol) (final concentration 6 µM) and 1,2-dioleyolglycerol (final concentration 3 µM) were mixed and dried under a stream of nitrogen. To the lipids was added 50 mM Hepes pH 7.5 (2× final concentration of lipids) and the suspension was sonicated for 3 min. at 4° C. To the suspension was added 50 mM Hepes pH 7.5, 300 mM NaCl, 2 mM DTT, 2 mM CaCl$_2$ and 2 mg/ml bovine serum albumin (BSA) (Sigma A7511) (1.2× final concentration of lipids). A typical assay consisted of the lipid mixture (85 µl) to which was added consecutively, the inhibitor (5 µl in DMSO) and cPLA$_2$, 10 ng for an automated system or 1 ng for a manual assay, in 10 µl of the BSA buffer. This assay was conducted by either the manual assay or automated assay protocol described below.

(b) Soluble Substrate Assay (LysoPC)

1-[$^{14}$C]-palmitoyl-2-hydroxyphosphotidyl-choline (57 mCi/mmol) (final concentration 4.4 µM) was dried under a stream of nitrogen. The lipid was resuspended by vortexing 80 mM Hepes pH 7.5, 1 mM EDTA (1.2×final concentration). A typical assay consisted of lipid suspension (85 µl) to which was added consecutively the inhibitor (5 µl in DMSO) and cPLA$_2$, 200 ng in 80 mM Hepes pH 7.5, 2 mM DTT and 1 M EDTA. This assay was conducted by either the manual assay or automated assay protocol described below.

(c) Automated Assay

The lipid suspension and inhibitor were pre-incubated for 7 min. at 37° C. Enzyme was added and the incubation was continued for a further 30 mins. The reaction was then quenched by the addition of decane: isopropanol: trifluoroacetic acid (192:8:1 w/v, 150 µl). A portion of the quench layer (50 µl) was passed through a Rainin Spheric-5 silica column (5 µ, 30×2.1 mm) eluting with heptane:methanol:TFA (97:3:0.1 v/v). The level of [$^{14}$C]-arachidonic acid was analyzed by an in-line Radiomatic Flo-One/Beta counter (Packard).

(d) Manual Assay

The lipid, inhibitor and enzyme mixture were incubated at 37° C. for 30 min. The reaction was quenched by the addition of heptane:isopropanol:0.5M sulfuric acid (105:20:1 v/v, 200 µl). Half of the quench layer was applied to a dispoable silica gel column (Whatman SIL, 1 ml) in a vacuum manifold positioned over a scintillation vial. Free [$^{14}$C]-arachidonic acid was eluted by the addition of ethyl ether (1 ml). The level of radioactivity was measured by liquid scintillation counter.

(e) PMN Assay

PMNs were isolated using Ficoll-Hypaque according to the manufacturers directions. Red blood cells contaminating the PMNs were removed by hypotonic lysis, and the PMN pellet was washed once, and resuspended in Hanks buffered saline at a concentration of 2×10$^6$ cells/ml. The cells were preincubated with inhibitors for 15 min at 37° C. and then stimulated with 2 µM A23187. When monitoring LTB$_4$ production as a measure of cPLA$_2$ inhibition, the reaction was quenched with an equal volume of ice cold phosphate buffered saline. Cells were removed by centrifugation, and the LTB$_4$ present in the cell supernatant was measured using the LTB$_4$ scintillation proximity assay provided by Amersham according to the manufacturers directions. In the assays reported in the Tables above, LTB$_4$ was measured. When monitoring arachidonic acid production, the reaction was quenched with methanol containing D8-arachidonic acid as an internal reference. The lipids were extracted by the method of Bligh et al. ((1959) Can. J. Biochem. Physiol., 37, 911–917), and the fatty acid was converted to the pentafluorobenzyl ester and analyzed by GC-MS in a manner similar to that reported by Ramesha and Taylor ((1991) Anal. Biochem. 192, 173–180).

References

Altschul, S. F., Madden, T. L., Schäffer, A. A., Zhang, J., Zhang, Z., Miller, W., and Lipman, D. J. (1997). Gapped BLAST and PSI-BLAST: a new generation of protein database search programs. Nucleic Acids Res. 25, 3389–3402.

Bacon, D. J., and Anderson, W. F. (1988). A fast algorithm for rendering space-filling molecule pictures. J. Mol. Graph. 6, 219–220.

Balboa, M. A., Balsinde, J., Jones, S. S., and Dennis, E. A. (1997). Identity between the Ca$^{2+}$-independent phsopholipase A$_2$ enzymes from P388D$_1$ macrophages and chinese hamster ovary cells. J. Biol. Chem. 272, 8576–8580.

Bonventre, J. V., Huang, Z., Reza Taheri, M., O'Leary, E., Li, E., Moskowitz, M. A., and Sapirstein, A. (1997) Reduced fertility and postischaemic brain injury in mice deficient in cytosolic phospholipase $A_2$. Nature 390, 622–625.

Börsch-Haubold, A. G., Bartoli, F., Asselin, J., Dudler, T., Kramer, R. M., Apitz-Castro, R., Watson, S. P., and Gelb, M. H. (1998). Identification of the phosphorylation sites of cytosolic phospholipase $A_2$ in agonist-stimulated human platelets and HeLa cells. J. Biol. Chem. 273, 4449–4458.

Bricogne, G. (1993). Direct phase determination by entropy maximization and likelihood ranking: status report and perspectives. Acta Cryst. D49, 37–60.

Brünger, A. T., Krukowski, A., and Erickson J. (1990) Slow-cooling protocols for crystallographic refinement by simulated annealing. Acta Cryst. A46, 585–593.

Brünger, A. T. (1992a). The free R value: a novel statistical quantity for assessing the accuracy of crystal structures. Nature 355, 472–474.

Brünger, A. T. (1992b). X-PLOR Version 3.1. A system for x-ray crystallography and NMR (New Haven: Yale University Press).

Clark, J. D., Lin, L.-L., Kriz, R. W., Ramesha, C. S., Sultzman, L. A., Lin, A. Y., Milona, N., and Knopf, J. L. (1991). A novel arachidonic acid-selective cytosolic $PLA_2$ contains a $Ca^{2+}$-dependent translocation domain with homology to PKC and GAP. Cell 65, 1043–1051.

Clark, J. D., Schievella, A. R., Nalefski, E. A., and Lin, L.-L. (1995). Cytosolic phospholipase $A_2$. J. Lipid Mediators Cell Signalling 12, 83–117.

Cleland, W. W., and Kreevoy, M. M. (1994). Low-barrier hydrogen bonds and enzymic catalysis. Science 264, 1887–1890.

Collaborative Computing Project Number 4 (1994). Acta Crystallogr. S760–763.

Cowtan, K. D. and Main, P. (1996). Phase combination and cross validation in iterated density modification calculations. Acta Crystallogr. D 42, 43–48.

Cygler, M. and Schrag, J. D. (1997). Structure as basis for understanding interfacial properties of lipases. Meth. Enzymol. 284, 3–27.

Dennis, E. A. (1997). The growing phospholipase $A_2$ superfamily of signal transduction enzymes. Trends Biochem. Sci. 22, 1–2.

De Carvalho, M. G. S., McCormack, A. L., Olson, E., Ghomaschi, F., Gelb, M., Yates III, J. R., and Leslie, C. C. (1996). Identification of phosphorylation sites of human 85 kda cytosolic phospholipase $A_2$ expressed in insect cells and present in human monocytes. J. Biol. Chem. 271, 1–11.

De La Fortelle, E., and Bricogne, G. (1997). Maximum-likelihood heavy-atom parameter refinement for multiple isomorphous replacement and multiwavelength anomalous diffraction methods. Methods Enzymol. 276, 494–523.

Derewenda, Z. S, and Derewenda, U. (1991). Relationships among serine hydrolases: evidence for a common structural motif in triacylglyceride lipases and esterases. Biochem. Cell. Biol. 69, 842–851.

Duggleby, H. J., Tolley, S. P., Hill, C. P., Dodson, E. J., Dodson, G., and Moody, P. C. E. (1995). Penicillin acylase has a single-amino-acid catalytic centre. Nature 373, 264–268.

Essen, L.-O., Perisic, O., Cheung, R., Katan, M., & Williams, R. L. (1996). Crystal structure of a mammalian phosphoinositide-specific phospholipase C. Nature 380, 595–602.

Glover, S., de Carvalho, M., Bayburt, T., Jonas, M., Chi, E., Leslie, E., and Gelb, M. (1995) Translocation of the 85-kDa phospholipase $A_2$ from cytosol to the nuclear envelope in rat basophilic leukemia cells stimulated with calcium ionophore or IgE/antigen. J. Biol. Chem. 270, 15359–15367.

Grobler, J. A., Essen, L.-O., Williams, R. L., and Hurley, J. H. (1996). C2 domain conformational changes in phospholipase C. Nat. Struct. Biol. 3, 788–795.

Hanel, A. M., and Gelb, M. H. (1993). Processive interfacial catalysis by mammalian 85-kilodalton phospholipase $A_2$ enzymes on product-containing vesicles: application to the determination of substrate, preferences. Biochemistry 32, 5949–5958.

Hanel, A. M., and Gelb, M. H. (1995). Multiple enzymatic activities of the human cytosolic 85-kDa phospholipase $A_2$: hydrolytic reactions and acyl transfer to glycerol. Biochemistry 34, 7807–7818.

Hattori, M., Adachi, H., Tsujimoto, M., Arai, H., and Inoue, K. (1994). The catalytic subunit of bovine brain platelet-activating factor acetylhydrolase is a novel type of serine esterase. J. Biol. Chem. 269, 23150–23155.

Hattori, M., Adachi, H., Aoki, J., Tsujimoto, M., Arai, H., and Inoue, K. (1995). Cloning and expression of a cDNA encoding the beta-subunit (30-kDa subunit) of bovine brain platelet-activating factor acetylhydrolase. J. Biol. Chem. 270, 31345–31352.

Hendrickson, W. A. (1991). Determination of macromolecular structures from anomalous diffraction of synchrotron radiation. Science 254, 51–58.

Hixon, M. S., Ball, A., and Gelb, M. H. (1998). Calcium-dependent and—independent interfacial binding and catalysis of cytosolic group IV phospholipase $A_2$. Biochemistry 37, 8516–8526.

Huang, Z., Payette, P., Abdullah, K., Cromlish, W. A., and Kennedy, B. P. (1996). Functional identification of the active-site nucleophile of the human 85-kDa cytosolic phospholipase $A_2$. Biochemistry 35, 3712–3721.

Kramer, R. M., Roberts, E. F., Manetta, J., and Putnam, J. E. (1991). The $Ca^{2+}$-sensitive cytosolic phospholipase $A_2$ is a 100-kDA protein in human monoblast U937 cells. J. Biol. Chem. 266, 5268–5272.

Kraulis, P. J. (1991). MOLSCRIPT: a program to produce both detailed and schematic plots of protein structures. J. Appl. Cryst. 24, 946–950.

Leslie, C. C. and Channon, J. Y. (1990). Anionic phospholipids stimulate an arachidonoyl-hydrolyzing phospholipase $A_2$ from macrophages and reduce the calcium requirement for activity. Biochim. Biophys. Acta 1045, 261–270.

Leslie, C. C. (1997). Properties and regulation of cytosolic phospholipase $A_2$. J. Biol. Chem. 272, 16709–16712.

Lin, L.-L., Lin, A. Y., and DeWitt, D. L. (1992a) IL-1 induces the accumulation of $cPLA_2$ and the release of $PGE_2$ in human fibroblasts. J. Biol. Chem. 267, 23451–23454.

Lin, L.-L., Lin, A. Y., and Knopf, J. L. (1992b) Cytosolic phospholipase $A_2$ is coupled to hormonally regulated release of arachidonic acid. Proc. Natl. Acad. Sci. USA 89, 6147–6151.

Lin, L.-L., Wartmann, M., Lin, A. Y., Knopf, J. L., Seth, A., and Davis, R. J. (1993) $cPLA_2$ is phosphorylated and activated by MAP kinase. Cell 72, 269–278.

Matagne, A., Lamotte-Brasseur, J., and Frère, J.-M. (1998). Catalytic properties of class A-lactamases: efficiency and diversity. Biochem. J. 330, 581–598.

Mosior, M., Six, D. A., and Dennis, E. A. (1998). Group IV cytosolic phospholipase $A_2$ binds with high affinity and specificity to phosphatidylinositol 4,5-bisphosphate resulting in dramatic increases in activity. J. Biol. Chem. 273, 2184–2191.

Murshudov, G. N., Vagin, A. A., and Dodson, E. J. (1997) Acta Crystallogr. Sect. D. 53, 240–255.

Nalefski, E. A., Sultzman, L. A., Martin, D. M., Kriz, R. W., Towler, P. S., Knopf, J. L., and Clark, J. D. (1994) Delineation of two functionally distinct domains of cytosolic phospholipase $A_2$, a regulatory $Ca^{2+}$-dependent lipid-binding domain and a $Ca^{2+}$-independent catalytic domain. J. Biol. Chem. 269, 18239–18249.

Nalefski, E. A., and Falke, J. J. (1996). The C2 domain calcium-binding motif: structural and functional diversity. Protein Sci. 12, 2375–2390.

Nalefski, E. A., McDonagh, T., Somers, W., Seehra, J., Falke, J. J., and Clark, J. D. (1998). Independent folding and ligand specificity of the C2 calcium-dependent lipid binding domain of cytosolic phospholipase $A_2$. J. Biol. Chem. 273, 1365–1372.

Nalefski, E. A., and Falke, J. J. (1998). Location of the membrane-docking face on the $Ca^{2+}$-activated C2 domain of cytosolic phospholipase $A_2$. Biochemistry 37, 17642–17650.

Nicholls, A. (1992). GRASP: Graphical representation and analysis of surface properties (Columbia University, New York).

O'Byrne, P. M. (1997) Leukotrienes in the pathogenesis of asthma. Chest 111, 27S–34S.

Otwinowski, Z. (1993). In Data Collection and Processing. L. Sawyer, N. Isaacs, and S. W. Bailey, eds. (Daresbury, U. K.: Science and Engineering Council),pp. 56–62.

Perisic, O., Fong, S., Lynch, D. E., Bycroft, M., & Williams, R. L. (1998). Crystal structure of a calcium-phospholipid binding domain from cytosolic phospholipase $A_2$. J. Biol. Chem. 273, 1596–1604.

Pickard, R. T., Chiou, X. G., Strifler, B. A., DeFelippis, M. R., Hyslop, P. A., Tebbe, A. L., Yee, Y., K., Reynolds, L. J., Dennis, E. A., Kramer, R. M., & Sharp, J. D. (1996). Identification of essential residues for the catalytic function of 85-dKa cytosolic phospholipase $A_2$. J. Biol. Chem. 271, 19225–19231.

Qiu, Z.-H., Gijón, M. A., de Carvalho, M. S., Spencer, D. M., and Leslie, C. C. (1998). The role of calcium and phosphorylation of cytosolic phospholipase $A_2$ in regulating arachidonic acid release in macrophages. J. Biol. Chem. 273, 8203–8211.

Rao, V. D., Misna, S., Boronekov, I. V., Anderson, R. A., and Hurley, J. H. (1998). Structure of type IIbeta phosphatidylinositol phosphate kinase: a protein kinase fold flattened for interfacial phosphorylation. Cell 94, 829–839.

Reynolds, L. J., Hughes, L. L., Louis, A. I., Kramer, R. M., and Dennis, E. A. (1993). Metal ion and salt effects on the phospholipase $A_2$ lysophospholipase, and transacylase activities of human cytosolic phospholipase $A_2$. Biochim. Biophys. Acta 1167, 272–280.

Schievella, A. R., Regier, M. K., Smith, W. L., and Lin, L.-L. (1995). Calcium-mediated translocation of cytosolic phospholipase $A_2$ to the nuclear envelope and endoplasmic reticulum. J. Biol. Chem. 270, 30749–30754.

Schrag, J. D. and Cyger, M. (1997). Lipases and hydrolase fold. Meth. Enzymol. 284, 85–107.

Scott, D. L., White, S. P., Zbyszed, O., Yan, W., Gelb, M. H., and Sigler, P. B. (1990). Interfacial catalysis: the mechanism of phospholipase $A_2$. Science 250, 1541–1546.

Sharp, J. D., White, D. L., Chiou, X. G., Goodson, T., Gamboa, G. C., McClure, D., Burgett, S., Hoskins, J., Skatrud, P. L., Sportsman, J. R., Becker, G. W., Kang, L. H., Roberts, E. F., and Kramer, R. M. (1991). Molecular cloning and expression of human $Ca^{2+}$-sensitive cytosolic phospholipase $A_2$. J. Biol. Chem. 266, 14850–14853.

Sharp, J. D., Pickard, R. T., Chiou, X. G., Manetta, J. V., Kovacevic, S., Miller, J. R., Varshavsky, A. D., Roberts, E. F., Strifler, B. A., Brems, D. N. et al. (1994). Serine 228 is essential for catalytic activities of 85-kDa cytosolic phospholipase $A_2$. J. Biol. Chem. 269, 23250–23254.

Simon, L. S., Lanza, F. L., Lipsky, P. E., Hubbard, R. C., Talwalker, S., Schwartz, B. D., Isakson, P. C., and Geis, G. S. (1998). Preliminary study of the safety and efficacy of SC-58635, a novel cyclooxygenase 2 inhibitor: efficacy and safety in two placebo-controlled trials in osteoarthritis and rheumatoid arthritis, and studies of gastrointestinal and platelet effects. Arthritis Rheum. 41, 1591–1602.

Tang, J., Kriz, R. W., Wolfman, N., Shaffer, M., Seehra, J., and Jones, S. S. (1997). A novel cytosolic calcium-independent phsopholipase $A_2$ contains eight ankyrin motifs. J. Biol. Chem. 272, 8567–8575.

Tjoelker, L. W., Wilder, C., Eberhardt, C., Stafforini, D. M., Dietsch, G., Schimpf, B., Hooper, S., Le Trong, H., Cousens, L. S., Zimmerman, G. A., et al. (19950. Anti-inflammatory properties of a platelet-activating factor acetylhydrolase. Nature 374, 549–553.

Trimble, L. A., Street, I. P., Perrier, H., Tremblay, N. M., Weech, P. K., and Bernstein, M. A. (1993). NMR structural studies of the tight complex between a trifluoromethyl ketone inhibitor and the 85-kDa human phospholipase $A_2$. Biochemistry 32, 12560–12565.

Underwood, K. W., Song, C., Kriz, R. W., Chang, X. J., Knopf, J. L. & Lin, L.-L. (1998). A novel calcium-independent phospholipase $A_2$, cPLA2-, that is prenylated and contains homology to cPLA2. J. Biol. Chem. 273, 21926–21932.

Uozumi, N., Kume, K., Nagase, T., Nakatani, N., Ishii, S., Tashiro, F., Komagata, Y., Maki, K., Ikuta, K., Ouchi, Y., Miyazaki, J-i., & Shimizu, T. (1997). Role of cytosolic phospholipase $A_2$ in allergic response and parturition. Nature 390, 618–622.

Venable, M. E., Olson, S. C., Nieto, M. L., and Wykle, R. L. (1993). Enzymatic studies of lyso platelet-activating factor acylation in human neutrophils and changes upon stimulation. J. Biol Chem 268, 7965–7975.

Xu, G.-Y., McDonagh, T., Yu, H.-A., Nalefski, E., Clark, J. D., & Cumming, D. A. (1998). Solution structure and membrane interactions of the C2 domain of cytosolic phospholipase $A_2$. J. Mol. Biol. 280, 485–500.

All references cited herein are incorporated herein by reference as if fully set forth.

What is claimed is:

1. A method of identifying an inhibitors of cPLA$_2$ activity comprising:
   (a) providing a compound;
   (b) identifying whether the compound interacts with one or more atoms of one or more amino acids in the cPLA$_2$ active site, and wherein said one or more atoms is selected from the group consisting of:
   CB and Oγ atoms of Ser228;
   Oδ1 and Oδ2 atoms of Asp549 and Asp575;
   CB, CG, CD, NE, CZ, NH1 and NH2 atoms of Arg200, Arg413 and Arg579;
   Backbone carbonyl oxygen of Trp393;
   Nδ2 and Oδ1 atoms of Asn555;
   Atoms CD1, CE1, CG, CZ, CE2 and CD2 of Phe397, Phe681, Phe683 and Phe199;
   CG, CD1, NE1, CE2, CZ2, CH2, CZ3, CE3 and CD2 of Trp232 and Trp393;
   CB and Oγ atoms of Ser577;
   Atoms CB and Sγ of Cys331;
   Atoms OE1 and OE2 of Glu589;
   Atoms CB, CG, CD, CE and NZ of Lys588;
   Oγ1 atom of Thr680;
   OE1 and OE2 atoms of Glu418 and Glu422;
   Atoms CB, CG, SD and CE of Mer417;
   Atoms CB, CG, CD1 and CD2 of Leu400 and Leu421;
   Atoms CB, CG1, CG2, or CD1 of Ile424;
   Backbone NH and carbonyl oxygen atoms of Ala578; and
   Atoms CB, CG, ND1, CE1, NE2, and CD2 of His639; and
   (c) assaying the ability of the compound to inhibit cPLA$_2$ activity, thereby identifying an inhibitor of cPLA$_2$ activity.

2. The method of claim 1, wherein said activity of cPLA$_2$ is phospholipid metabolism.

3. The method of claim 1, wherein said activity of cPLA$_2$ is membrane binding.

4. The method of claim 1, wherein said activity of cPLA$_2$ is cleavage of the sn-2 ester of a glycerophospholipididic substrate.

5. The method of claim 1, wherein the identified inhibitor has an IC$_{50}$ value of less than about 25 µM in a soluble substrate assay.

6. The method of claim 1, wherein the identified inhibitor has an IC$_{50}$ value of less than about 5 µM in a vesicle assay.

7. The method of claim 1, wherein the identified inhibitor has an IC$_{50}$ value of less than about 1 µM in a PMN assay.

* * * * *

SEQUENCE LISTING

<160> NUMBER OF SEQ ID NOS: 3

<210> SEQ ID NO 1
<211> LENGTH: 2247
<212> TYPE: DNA
<213> ORGANISM: Homo sapiens
<220> FEATURE:
<221> NAME/KEY: CDS
<222> LOCATION: (1)..(2247)

<400> SEQUENCE: 1

```
atg tca ttt ata gat cct tac cag cac att ata gtg gag cac cag tat      48
Met Ser Phe Ile Asp Pro Tyr Gln His Ile Ile Val Glu His Gln Tyr
 1               5                  10                  15 tcc cac aag ttt acg gta gtg gtg tta cgt gcc acc aaa gtg aca aag      96
Ser His Lys Phe Thr Val Val Val Leu Arg Ala Thr Lys Val Thr Lys
             20                  25                  30 ggg gcc ttt ggt gac atg ctt gat act cca gat ccc tat gtg gaa ctt     144
Gly Ala Phe Gly Asp Met Leu Asp Thr Pro Asp Pro Tyr Val Glu Leu
         35                  40                  45 ttt atc tct aca acc cct gac agc agg aag aga aca aga cat ttc aat     192
Phe Ile Ser Thr Thr Pro Asp Ser Arg Lys Arg Thr Arg His Phe Asn
     50                  55                  60 aat gac ata aac cct gtg tgg aat gag acc ttt gaa ttt att ttg gat     240
Asn Asp Ile Asn Pro Val Trp Asn Glu Thr Phe Glu Phe Ile Leu Asp
 65                  70                  75                  80 cct aat cag gaa aat gtt ttg gag att acg tta atg gat gcc aat tat     288
Pro Asn Gln Glu Asn Val Leu Glu Ile Thr Leu Met Asp Ala Asn Tyr
                 85                  90                  95 gtc atg gat gaa act cta ggg aca gca aca ttt act gta tct tct atg     336
Val Met Asp Glu Thr Leu Gly Thr Ala Thr Phe Thr Val Ser Ser Met
            100                 105                 110 aag gtg gga gaa aag aaa gaa gtt cct ttt att ttc aac caa gtc act     384
Lys Val Gly Glu Lys Lys Glu Val Pro Phe Ile Phe Asn Gln Val Thr
        115                 120                 125 gaa atg gtt cta gaa atg tct ctt gaa gtt tgc tca tgc cca gac cta     432
Glu Met Val Leu Glu Met Ser Leu Glu Val Cys Ser Cys Pro Asp Leu
    130                 135                 140 cga ttt agt atg gct ctg tgt gat cag gag aag act ttc aga caa cag     480
Arg Phe Ser Met Ala Leu Cys Asp Gln Glu Lys Thr Phe Arg Gln Gln
145                 150                 155                 160 aga aaa gaa cac ata agg gag agc atg aag aaa ctc ttg ggt cca aag     528
Arg Lys Glu His Ile Arg Glu Ser Met Lys Lys Leu Leu Gly Pro Lys
                165                 170                 175 aat agt gaa gga ttg cat tct gca cgt gat gtg cct gtg gta gcc ata     576
Asn Ser Glu Gly Leu His Ser Ala Arg Asp Val Pro Val Val Ala Ile
            180                 185                 190 ttg ggt tca ggt ggg ggt ttc cga gcc atg gtg gga ttc tct ggt gtg     624
Leu Gly Ser Gly Gly Gly Phe Arg Ala Met Val Gly Phe Ser Gly Val
        195                 200                 205 atg aag gca tta tac gaa tca gga att ctg gat tgt gct acc tac gtt     672
Met Lys Ala Leu Tyr Glu Ser Gly Ile Leu Asp Cys Ala Thr Tyr Val
    210                 215                 220 gct ggt ctt tct ggc tcc acc tgg tat atg tca acc ttg tat tct cac     720
Ala Gly Leu Ser Gly Ser Thr Trp Tyr Met Ser Thr Leu Tyr Ser His
225                 230                 235                 240 cct gat ttt cca gag aaa ggg cca gag gag att aat gaa gaa cta atg     768
Pro Asp Phe Pro Glu Lys Gly Pro Glu Glu Ile Asn Glu Glu Leu Met
                245                 250                 255
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aaa | aat | gtt | agc | cac | aat | ccc | ctt | tta | ctt | ctc | aca | cca | cag | aaa | gtt | 816  |
| Lys | Asn | Val | Ser | His | Asn | Pro | Leu | Leu | Leu | Leu | Thr | Pro | Gln | Lys | Val |      |
|     |     |     | 260 |     |     |     | 265 |     |     |     | 270 |     |     |     |     |      |
| aaa | aga | tat | gtt | gag | tct | tta | tgg | aag | aag | aaa | agc | tct | gga | caa | cct | 864  |
| Lys | Arg | Tyr | Val | Glu | Ser | Leu | Trp | Lys | Lys | Lys | Ser | Ser | Gly | Gln | Pro |      |
|     |     | 275 |     |     |     | 280 |     |     |     | 285 |     |     |     |     |     |      |
| gtc | acc | ttt | act | gat | atc | ttt | ggg | atg | tta | ata | gga | gaa | aca | cta | att | 912  |
| Val | Thr | Phe | Thr | Asp | Ile | Phe | Gly | Met | Leu | Ile | Gly | Glu | Thr | Leu | Ile |      |
| 290 |     |     |     |     | 295 |     |     |     |     | 300 |     |     |     |     |     |      |
| cat | aat | aga | atg | aat | act | act | ctg | agc | agt | ttg | aag | gaa | aaa | gtt | aat | 960  |
| His | Asn | Arg | Met | Asn | Thr | Thr | Leu | Ser | Ser | Leu | Lys | Glu | Lys | Val | Asn |      |
| 305 |     |     |     | 310 |     |     |     |     | 315 |     |     |     |     | 320 |     |      |
| act | gca | caa | tgc | cct | tta | cct | ctt | ttc | acc | tgt | ctt | cat | gtc | aaa | cct | 1008 |
| Thr | Ala | Gln | Cys | Pro | Leu | Pro | Leu | Phe | Thr | Cys | Leu | His | Val | Lys | Pro |      |
|     |     |     | 325 |     |     |     | 330 |     |     |     | 335 |     |     |     |     |      |
| gac | gtt | tca | gag | ctg | atg | ttt | gca | gat | tgg | gtt | gaa | ttt | agt | cca | tac | 1056 |
| Asp | Val | Ser | Glu | Leu | Met | Phe | Ala | Asp | Trp | Val | Glu | Phe | Ser | Pro | Tyr |      |
|     |     | 340 |     |     |     | 345 |     |     |     | 350 |     |     |     |     |     |      |
| gaa | att | ggc | atg | gct | aaa | tat | ggt | act | ttt | atg | gct | ccc | gac | tta | ttt | 1104 |
| Glu | Ile | Gly | Met | Ala | Lys | Tyr | Gly | Thr | Phe | Met | Ala | Pro | Asp | Leu | Phe |      |
| 355 |     |     |     |     | 360 |     |     |     |     | 365 |     |     |     |     |     |      |
| gga | agc | aaa | ttt | ttt | atg | gga | aca | gtc | gtt | aag | aag | tat | gaa | gaa | aac | 1152 |
| Gly | Ser | Lys | Phe | Phe | Met | Gly | Thr | Val | Val | Lys | Lys | Tyr | Glu | Glu | Asn |      |
| 370 |     |     |     | 375 |     |     |     |     | 380 |     |     |     |     |     |     |      |
| ccc | ttg | cat | ttc | tta | atg | ggt | gtc | tgg | ggc | agt | gcc | ttt | tcc | ata | ttg | 1200 |
| Pro | Leu | His | Phe | Leu | Met | Gly | Val | Trp | Gly | Ser | Ala | Phe | Ser | Ile | Leu |      |
| 385 |     |     |     | 390 |     |     |     |     | 395 |     |     |     |     | 400 |     |      |
| ttc | aac | aga | gtt | ttg | ggc | gtt | tct | ggt | tca | caa | agc | aga | ggc | tcc | aca | 1248 |
| Phe | Asn | Arg | Val | Leu | Gly | Val | Ser | Gly | Ser | Gln | Ser | Arg | Gly | Ser | Thr |      |
|     |     |     | 405 |     |     |     |     | 410 |     |     |     | 415 |     |     |     |      |
| atg | gag | gaa | gaa | tta | gaa | aat | att | acc | aca | aag | cat | att | gtg | agt | aat | 1296 |
| Met | Glu | Glu | Glu | Leu | Glu | Asn | Ile | Thr | Thr | Lys | His | Ile | Val | Ser | Asn |      |
|     | 420 |     |     |     |     | 425 |     |     |     |     | 430 |     |     |     |     |      |
| gat | agc | tcg | gac | agt | gat | gat | gaa | tca | cac | gaa | ccc | aaa | ggc | act | gaa | 1344 |
| Asp | Ser | Ser | Asp | Ser | Asp | Asp | Glu | Ser | His | Glu | Pro | Lys | Gly | Thr | Glu |      |
|     |     | 435 |     |     |     |     | 440 |     |     |     |     | 445 |     |     |     |      |
| aat | gaa | gat | gct | gga | agt | gac | tat | caa | agt | gat | aat | caa | gca | agt | tgg | 1392 |
| Asn | Glu | Asp | Ala | Gly | Ser | Asp | Tyr | Gln | Ser | Asp | Asn | Gln | Ala | Ser | Trp |      |
|     | 450 |     |     |     |     | 455 |     |     |     |     | 460 |     |     |     |     |      |
| att | cat | cgt | atg | ata | atg | gcc | ttg | gtg | agt | gat | tca | gct | tta | ttc | aat | 1440 |
| Ile | His | Arg | Met | Ile | Met | Ala | Leu | Val | Ser | Asp | Ser | Ala | Leu | Phe | Asn |      |
| 465 |     |     |     | 470 |     |     |     |     | 475 |     |     |     |     | 480 |     |      |
| acc | aga | gaa | gga | cgt | gct | ggg | aag | gta | cac | aac | ttc | atg | ctg | ggc | ttg | 1488 |
| Thr | Arg | Glu | Gly | Arg | Ala | Gly | Lys | Val | His | Asn | Phe | Met | Leu | Gly | Leu |      |
|     |     |     |     | 485 |     |     |     |     | 490 |     |     |     |     | 495 |     |      |
| aat | ctc | aat | aca | tct | tat | cca | ctg | tct | cct | ttg | agt | gac | ttt | gcc | aca | 1536 |
| Asn | Leu | Asn | Thr | Ser | Tyr | Pro | Leu | Ser | Pro | Leu | Ser | Asp | Phe | Ala | Thr |      |
|     |     |     | 500 |     |     |     | 505 |     |     |     | 510 |     |     |     |     |      |
| cag | gac | tcc | ttt | gat | gat | gat | gaa | ctg | gat | gca | gct | gta | gca | gat | cct | 1584 |
| Gln | Asp | Ser | Phe | Asp | Asp | Asp | Glu | Leu | Asp | Ala | Ala | Val | Ala | Asp | Pro |      |
|     |     | 515 |     |     |     |     | 520 |     |     |     |     | 525 |     |     |     |      |
| gat | gaa | ttt | gag | cga | ata | tat | gag | cct | ctg | gat | gtc | aaa | agt | aaa | aag | 1632 |
| Asp | Glu | Phe | Glu | Arg | Ile | Tyr | Glu | Pro | Leu | Asp | Val | Lys | Ser | Lys | Lys |      |
|     |     | 530 |     |     |     |     | 535 |     |     |     |     | 540 |     |     |     |      |
| att | cat | gta | gtg | gac | agt | ggg | ctc | aca | ttt | aac | ctg | ccg | tat | ccc | ttg | 1680 |
| Ile | His | Val | Val | Asp | Ser | Gly | Leu | Thr | Phe | Asn | Leu | Pro | Tyr | Pro | Leu |      |
| 545 |     |     |     |     | 550 |     |     |     |     | 555 |     |     |     |     | 560 |      |
| ata | ctg | aga | cct | cag | aga | ggg | gtt | gat | ctc | ata | atc | tcc | ttt | gac | ttt | 1728 |
| Ile | Leu | Arg | Pro | Gln | Arg | Gly | Val | Asp | Leu | Ile | Ile | Ser | Phe | Asp | Phe |      |
|     |     |     |     | 565 |     |     |     |     | 570 |     |     |     |     | 575 |     |      |

```
tct gca agg cca agt gac tct agt cct ccg ttc aag gaa ctt cta ctt    1776
Ser Ala Arg Pro Ser Asp Ser Ser Pro Pro Phe Lys Glu Leu Leu Leu
        580                 585                 590 gca gaa aag tgg gct aaa atg aac aag ctc ccc ttt cca aag att gat    1824
Ala Glu Lys Trp Ala Lys Met Asn Lys Leu Pro Phe Pro Lys Ile Asp
    595                 600                 605 cct tat gtg ttt gat cgg gaa ggg ctg aag gag tgc tat gtc ttt aaa    1872
Pro Tyr Val Phe Asp Arg Glu Gly Leu Lys Glu Cys Tyr Val Phe Lys
610                 615                 620 ccc aag aat cct gat atg gag aaa gat tgc cca acc atc atc cac ttt    1920
Pro Lys Asn Pro Asp Met Glu Lys Asp Cys Pro Thr Ile Ile His Phe
625                 630                 635                 640 gtt ctg gcc aac atc aac ttc aga aag tac aag gct cca ggt gtt cca    1968
Val Leu Ala Asn Ile Asn Phe Arg Lys Tyr Lys Ala Pro Gly Val Pro
                645                 650                 655 agg gaa act gag gaa gag aaa gaa atc gct gac ttt gat att ttt gat    2016
Arg Glu Thr Glu Glu Glu Lys Glu Ile Ala Asp Phe Asp Ile Phe Asp
            660                 665                 670 gac cca gaa tca cca ttt tca acc ttc aat ttt caa tat cca aat caa    2064
Asp Pro Glu Ser Pro Phe Ser Thr Phe Asn Phe Gln Tyr Pro Asn Gln
        675                 680                 685 gca ttc aaa aga cta cat gat ctt atg cac ttc aat act ctg aac aac    2112
Ala Phe Lys Arg Leu His Asp Leu Met His Phe Asn Thr Leu Asn Asn
    690                 695                 700 att gat gtg ata aaa gaa gcc atg gtt gaa agc att gaa tat aga aga    2160
Ile Asp Val Ile Lys Glu Ala Met Val Glu Ser Ile Glu Tyr Arg Arg
705                 710                 715                 720 cag aat cca tct cgt tgc tct gtt tcc ctt agt aat gtt gag gca aga    2208
Gln Asn Pro Ser Arg Cys Ser Val Ser Leu Ser Asn Val Glu Ala Arg
                725                 730                 735 aga ttt ttc aac aag gag ttt cta agt aaa ccc aaa gca                2247
Arg Phe Phe Asn Lys Glu Phe Leu Ser Lys Pro Lys Ala
            740                 745

<210> SEQ ID NO 2
<211> LENGTH: 749
<212> TYPE: PRT
<213> ORGANISM: Homo sapiens

<400> SEQUENCE: 2

Met Ser Phe Ile Asp Pro Tyr Gln His Ile Ile Val Glu His Gln Tyr
1               5                   10                  15

Ser His Lys Phe Thr Val Val Leu Arg Ala Thr Lys Val Thr Lys
            20                  25                  30

Gly Ala Phe Gly Asp Met Leu Asp Thr Pro Asp Pro Tyr Val Glu Leu
        35                  40                  45

Phe Ile Ser Thr Thr Pro Asp Ser Arg Lys Arg Thr Arg His Phe Asn
    50                  55                  60

Asn Asp Ile Asn Pro Val Trp Asn Glu Thr Phe Glu Phe Ile Leu Asp
65                  70                  75                  80

Pro Asn Gln Glu Asn Val Leu Glu Ile Thr Leu Met Asp Ala Asn Tyr
                85                  90                  95

Val Met Asp Glu Thr Leu Gly Thr Ala Thr Phe Thr Val Ser Ser Met
            100                 105                 110

Lys Val Gly Glu Lys Lys Glu Val Pro Phe Ile Phe Asn Gln Val Thr
        115                 120                 125

Glu Met Val Leu Glu Met Ser Leu Glu Val Cys Ser Cys Pro Asp Leu
    130                 135                 140
```

-continued

```
Arg Phe Ser Met Ala Leu Cys Asp Gln Glu Lys Thr Phe Arg Gln Gln
145                 150                 155                 160

Arg Lys Glu His Ile Arg Glu Ser Met Lys Lys Leu Leu Gly Pro Lys
                165                 170                 175

Asn Ser Glu Gly Leu His Ser Ala Arg Asp Val Pro Val Val Ala Ile
                180                 185                 190

Leu Gly Ser Gly Gly Phe Arg Ala Met Val Gly Phe Ser Gly Val
            195                 200                 205

Met Lys Ala Leu Tyr Glu Ser Gly Ile Leu Asp Cys Ala Thr Tyr Val
210                 215                 220

Ala Gly Leu Ser Gly Ser Thr Trp Tyr Met Ser Thr Leu Tyr Ser His
225                 230                 235                 240

Pro Asp Phe Pro Glu Lys Gly Pro Glu Glu Ile Asn Glu Glu Leu Met
                245                 250                 255

Lys Asn Val Ser His Asn Pro Leu Leu Leu Thr Pro Gln Lys Val
                260                 265                 270

Lys Arg Tyr Val Glu Ser Leu Trp Lys Lys Ser Ser Gly Gln Pro
    275                 280                 285

Val Thr Phe Thr Asp Ile Phe Gly Met Leu Ile Gly Glu Thr Leu Ile
290                 295                 300

His Asn Arg Met Asn Thr Thr Leu Ser Ser Leu Lys Glu Lys Val Asn
305                 310                 315                 320

Thr Ala Gln Cys Pro Leu Pro Leu Phe Thr Cys Leu His Val Lys Pro
                325                 330                 335

Asp Val Ser Glu Leu Met Phe Ala Asp Trp Val Glu Phe Ser Pro Tyr
                340                 345                 350

Glu Ile Gly Met Ala Lys Tyr Gly Thr Phe Met Ala Pro Asp Leu Phe
            355                 360                 365

Gly Ser Lys Phe Phe Met Gly Thr Val Val Lys Lys Tyr Glu Glu Asn
    370                 375                 380

Pro Leu His Phe Leu Met Gly Val Trp Gly Ser Ala Phe Ser Ile Leu
385                 390                 395                 400

Phe Asn Arg Val Leu Gly Val Ser Gly Ser Gln Ser Arg Gly Ser Thr
                405                 410                 415

Met Glu Glu Glu Leu Glu Asn Ile Thr Thr Lys His Ile Val Ser Asn
                420                 425                 430

Asp Ser Ser Asp Ser Asp Asp Glu Ser His Glu Pro Lys Gly Thr Glu
                435                 440                 445

Asn Glu Asp Ala Gly Ser Asp Tyr Gln Ser Asp Asn Gln Ala Ser Trp
450                 455                 460

Ile His Arg Met Ile Met Ala Leu Val Ser Asp Ser Ala Leu Phe Asn
465                 470                 475                 480

Thr Arg Glu Gly Arg Ala Gly Lys Val His Asn Phe Met Leu Gly Leu
                485                 490                 495

Asn Leu Asn Thr Ser Tyr Pro Leu Ser Pro Leu Ser Asp Phe Ala Thr
                500                 505                 510

Gln Asp Ser Phe Asp Asp Glu Leu Asp Ala Ala Val Ala Asp Pro
    515                 520                 525

Asp Glu Phe Glu Arg Ile Tyr Glu Pro Leu Asp Val Lys Ser Lys Lys
                530                 535                 540

Ile His Val Val Asp Ser Gly Leu Thr Phe Asn Leu Pro Tyr Pro Leu
545                 550                 555                 560
```

```
-continued

Ile Leu Arg Pro Gln Arg Gly Val Asp Leu Ile Ile Ser Phe Asp Phe
            565             570             575

Ser Ala Arg Pro Ser Asp Ser Ser Pro Pro Phe Lys Glu Leu Leu Leu
            580             585             590

Ala Glu Lys Trp Ala Lys Met Asn Lys Leu Pro Phe Pro Lys Ile Asp
        595             600             605

Pro Tyr Val Phe Asp Arg Glu Gly Leu Lys Glu Cys Tyr Val Phe Lys
        610             615             620

Pro Lys Asn Pro Asp Met Glu Lys Asp Cys Pro Thr Ile Ile His Phe
625             630             635             640

Val Leu Ala Asn Ile Asn Phe Arg Lys Tyr Lys Ala Pro Gly Val Pro
            645             650             655

Arg Glu Thr Glu Glu Glu Lys Glu Ile Ala Asp Phe Asp Ile Phe Asp
            660             665             670

Asp Pro Glu Ser Pro Phe Ser Thr Phe Asn Phe Gln Tyr Pro Asn Gln
        675             680             685

Ala Phe Lys Arg Leu His Asp Leu Met His Phe Asn Thr Leu Asn Asn
        690             695             700

Ile Asp Val Ile Lys Glu Ala Met Val Glu Ser Ile Glu Tyr Arg Arg
705             710             715             720

Gln Asn Pro Ser Arg Cys Ser Val Ser Leu Ser Asn Val Glu Ala Arg
            725             730             735

Arg Phe Phe Asn Lys Glu Phe Leu Ser Lys Pro Lys Ala
            740             745

<210> SEQ ID NO 3
<211> LENGTH: 5
<212> TYPE: PRT
<213> ORGANISM: Homo sapiens

<400> SEQUENCE: 3

Gly Leu Ser Gly Ser
 1               5
```